(12) United States Patent
Chue et al.

(10) Patent No.: US 8,865,935 B2
(45) Date of Patent: Oct. 21, 2014

(54) PURIFICATION METHODS FOR BETULONIC ACID AND BOC-LYSINATED BETULONIC ACID, AND ORGANIC SYNTHESIS OF BETULONIC ACID AMIDES WITH PIPERAZINE DERIVATIVES

(75) Inventors: Kuck-Tack Chue, Daejeon (KR); Tae-Hwan Kim, Daejeon (KR); Leonid Ten, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 0 days.

(21) Appl. No.: 14/126,898

(22) PCT Filed: Jun. 29, 2012

(86) PCT No.: PCT/KR2012/005154
§ 371 (c)(1),
(2), (4) Date: Dec. 17, 2013

(87) PCT Pub. No.: WO2013/002592
PCT Pub. Date: Jan. 3, 2013

(65) Prior Publication Data
US 2014/0243527 A1    Aug. 28, 2014

(30) Foreign Application Priority Data
Jun. 30, 2011   (KR) ................ 10-2011-0064883

(51) Int. Cl.
*C07J 63/00*    (2006.01)
(52) U.S. Cl.
CPC .................................... *C07J 63/008* (2013.01)
USPC ........................................ 562/498; 562/400
(58) Field of Classification Search
CPC ....................................................... C07J 63/00
USPC ................................................. 562/400, 498
See application file for complete search history.

(56) References Cited

U.S. PATENT DOCUMENTS

| 7,365,221 B2 * | 4/2008 | Allaway et al. ............... 560/116 |
| 2006/0154903 A1 | 7/2006 | Saxena et al. |
| 2010/0190795 A1 | 7/2010 | Yli-Kauhaluoma et al. |
| 2010/0196290 A1 | 8/2010 | Yli-Kauhaluoma et al. |
| 2010/0273801 A1 | 10/2010 | Yli-Kauhaluoma et al. |

FOREIGN PATENT DOCUMENTS

| KR | 10-0351704 B1 | 12/2002 |
| KR | 10-0376282 B1 | 9/2003 |
| KR | 10-0902846 B1 | 6/2009 |
| WO | WO 2006/050158 A2 | 5/2006 |
| WO | WO 2007/141398 A1 | 12/2007 |

OTHER PUBLICATIONS

Perumal Yogeeswari et al., "Betulinic Acid and Its Derivatives: a Review on their Biological Properties", Current Medicinal Chemistry, 2005, pp. 657-666, vol. 12.
Leonid Ten et al., "Extraction, crystallization, and continuous chromatographic processing for ultra pure betulin and high pure betulinic acid from birch barks", Theories and Applications of Chemical Engineering, 2010, pp. 1572, vol. 16.
A. N. Antimonova et al., "Synthesis of Betulonic Acid Amides", Chemistry of Natural Compounds, 2008, pp. 327-333, vol. 44, No. 3.
Emily Pisha et al., "Discovery of betulinic acid as a selective inhibitor of human melanoma that functions by induction of apoptosis", Nature Medicine, Oct. 1995, pp. 1046-1051, vol. 1 No. 10.
Toshihiro Fujioka et al., "Anti-Aids Agents, 11. Betulinic Acid and Platanic Acid as Anti-HIV Principles from *Syzigium claviflorum*, and the Anti-HIV Activity of Structurally Related Triterpenoids", Journal of Natural Products, Feb. 1994, pp. 243-247, vol. 57, No. 2.
Yunhao Gong et al., "The synergistic effects of betulin with acyclovir against herpes simplex viruses", Antiviral Research, 2004, pp. 127-130, vol. 64.
Jun'ichi Kobayashi et al., "Celogentins A-C, New Antimitotic Bicyclic Peptides from the Seeds of *Celosia argentea*", J. Org., Chem., 2001, pp. 6626-6633, vol. 66.
Xin Zhao et al., "Zipper-Featured δ-Peptide Foldamers Driven by Donor—Acceptor Interaction. Design, Synthesis, and Characterization", J. Org Chem., 2004, pp. 270-279, vol. 69.

* cited by examiner

*Primary Examiner* — Golam M M Shameem
(74) *Attorney, Agent, or Firm* — Rabin & Berdo, P.C.

(57) ABSTRACT

The present invention provides a method of purifying betulonic acid contained the reaction product of organic synthesis of a Jones oxidation reagent and betulin extracted from the bark of a birch, a method of preparing a piperazine betulonic acid amide derivative, which is used as a chemical having an antibacterial function, using the high-purity betulonic acid obtained by the purification method and a derivative prepared by this method, a method of purifying a Boc-lysinated betulonic acid monomer ester contained in the reaction product of organic synthesis of lysine and the high-purity betulonic acid (starting material) obtained by the purification method, and a method of purifying Boc-lysinated betulonic acid contained in the reaction product of hydrolysis of the high-purity Boc-lysinated betulonic acid monomer ester.

11 Claims, 7 Drawing Sheets

| No. | Name | RT[min] | area[mV*s] | [%] |
|---|---|---|---|---|
| 1 | | 3.5 | 147828 | 50.39 |
| 2 | | 4.1 | 9106 | 3.10 |
| 3 | | 5.28 | 2004 | 0.68 |
| 4 | Boc-Lys-BOA monomer ester | 12.03 | 23033 | 7.85 |
| 5 | | 15.15 | 95881 | 32.68 |
| 6 | | 16.08 | 8710 | 2.97 |
| 7 | | 23.23 | 6788 | 2.31 |

RT : Retention Time
Boc-Lys-BOA monomer ester: Boc-lysinated betulonic acid monomer ester

PURIFICATION METHODS FOR BETULONIC ACID AND BOC-LYSINATED BETULONIC ACID, AND ORGANIC SYNTHESIS OF BETULONIC ACID AMIDES WITH PIPERAZINE DERIVATIVES

TECHNICAL FIELD

The present invention relates to a method of purifying betuloinic acid, a method of preparing a piperazine betulonic acid amide derivative using high-purity betulonic acid and a derivative prepared by this method, and a method of purifying Boc-lysinated betulonic acid using high-purity betulonic acid. More particularly, the present invention relates to a method of purifying betulonic acid from the organic synthesis reaction product of a Jones oxidation reagent and betulin extracted from the bark of a birch, a method of preparing a piperazine betulonic acid amide derivative, which is used as a chemical having an antibacterial function, using the high-purity betulonic acid obtained by the purification method and a derivative prepared by this method, a method of purifying a Boc-lysinated betulonic acid monomer ester from the organic synthesis reaction product of lysine and the high-purity betulonic acid (starting material) obtained by the purification method, and a method of purifying Boc-lysinated betulonic acid from the hydrolysis reaction product of the high-purity Boc-lysinated betulonic acid monomer ester.

BACKGROUND ART

Betulin is used as a raw material for organic synthesis of betulinic acid, betulonic acid or derivatives thereof.

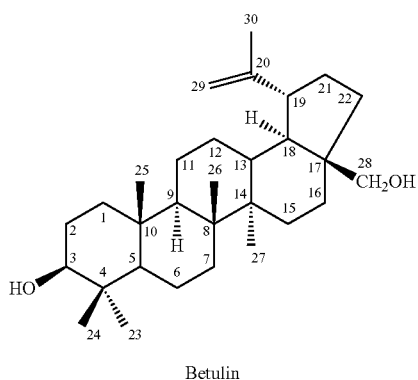

Betulin

It was scientifically discovered in the paper [Pisha, E. et al., (1995) J. M. nature Medicine, 1, 1046-1051] that betulinic acid has antitumor activity in melanomas (for example, MEL-2, MEL-2 and MEL-4).

Further, it was published in the paper [Fujioka, T. et al. (1994) J. Nat. Prod. 57, 243-247] that betulinic acid has anti-HIV activity in H9 lymphocytic cells.

Further, it was published in the paper [Yunhao Gong et al. Antiviral Research 64 (2004) 127-130] that betulin exhibits antiviral effects upon herpes simplex viruses when it is mixed with acyclovir.

Further, it was disclosed in PCT/US2005/039068 (WO2006/050158 A2) by GLINSKI that betulin ether derivatives were applied to functional cosmetics in order to obtain the effects of skin and hair protection in skin moisturizers, antiperspirants, anti-wrinkle treatment creams, hair depilatories and the like.

Moreover, the present inventors, P. Allaway et al., have recently insisted through U.S. Pat. No. 7,365,221B2 that monoacylated betulin and dihydrobetulin derivatives have potent anti-HIV activity.

Betuloinic acid is represented by the following Chemical Formula:

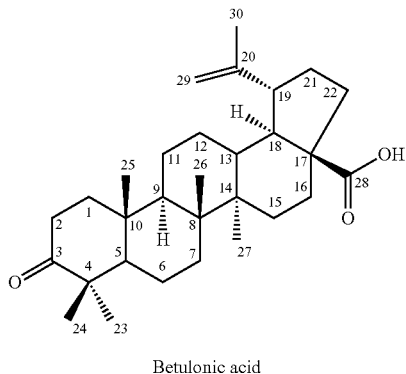

Betulonic acid

Betulonic acid is synthesized by Jones oxidation of betulin extracted from the bark of a birch using an organic solvent. Betulonic acid is not easily dissolved in a biocompatible solvent, but has useful biological characteristics such as anti-cancer activity, anti-inflammatory activity, etc.

Referring to related prior arts, it was disclosed in WO 2007/141398 A1 that derivatives of 28-eugenol ester betulonic acid, 28-aspartateamide dimethyl ester betulonic acid, 28-acetate betulonic acid and the like exhibit anti-microbial effects.

Further, it was disclosed in the papers [Kobayashi et al., J. Org. Chem. 66:6626-6623(2001)] and [Zhao et al., J. Org. Chem. 69:270-279(2004)] and Patent document [Saxena et al., US2006/0154903 A1] that betulonic acid amide derivatives are prepared by synthesis of betulonic acid and lysine. Here, these betulonic acid amide derivatives have attracted considerable attention since they were verified to have an effect of suppressing the growth of prostatic cancer cells (LNCaP, PC-3, DU-145). Boc-Lysinated betulonic acid monomer ester (referred to as Boc-Lys-BOA monomer ester) is obtained by organic synthesis of betulonic acid and Boc-Lys(Cbz)-OH, and Boc-Lysinated betulonic acid (referred to as Boc-Lys-BOA), which is known to have an effect on prostatic cancer cells in-vivo and in-vitro experiments thereof, is hydrolysis of betulonic acid and Boc-Lys(Cbz)-OH.

In order to use the above-mentioned derivatives and synthetic materials as medical drugs suitable for a human body, high-purity Boc-lysinated betulonic acid monomer ester and high-purity Boc-lysinated betulonic acid having a purity of 99% or more must be obtained by an advanced purification method for removing polar and nonpolar substances during a synthesis process. However, such an advanced purification method has not been proposed yet.

DISCLOSURE

Technical Problem

Accordingly, the present invention has been devised to solve the above-mentioned problems, and an object of the present invention is to provide an advanced purification method of producing high-purity betulonic acid from the organic synthesis reaction product of betulin and a Jones oxidation reagent.

Another object of the present invention is to provide a method of preparing a piperazine betulonic acid amide derivative having an antibacterial function using high-purity betulonic acid and a derivative prepared by this method.

A further object of the present invention is to provide a method of purifying a Boc-lysinated betulonic acid monomer ester by removing residual reactants and by-products from the organic synthesis reaction product of lysine and the high-purity betulonic acid (starting material) obtained by the advanced purification method, and a method of purifying Boc-lysinated betulonic acid from the hydrolysis reaction product of the high-purity Boc-lysinated betulonic acid monomer ester.

Technical Solution

In order to accomplish the above objects, an aspect of the present invention provides a method of purifying betulonic acid, including the steps of: a) injecting a Jones oxidation reagent ($CrO_3/c-H_2SO_4/H_2O$) into a mixed solution of acetone and betulin to obtain an organic synthesis reaction product and filtering and concentrating the obtained reaction product; b) introducing ethyl acetate into the concentrated reaction product to liquid-liquid extract betulonic acid; c) introducing a saturated aqueous sodium chloride solution (brine) into the ethyl acetate solution, in which the extracted betulonic acid is dissolved, to wash the ethyl acetate solution and remove impurities therefrom; d) introducing hexane or petroleum ether, as a nonpolar solvent, into the ethyl acetate solution to remove nonpolar substances, passing the washed ethyl acetate solution through an adsorption tower filled with aluminum oxide or silica gel, as a polar adsorbent, to remove polar substances, and then drying the ethyl acetate solution to produce betulonic acid (purity: more than 92%, yield to birch bark: 2.75 wt %); and e) dissolving the produced betulonic acid in a mixed solvent of ethanol and acetonitrile, separating and treating the mixed solution using a semi-preparative chromatography column filled with $C_{18}$ stationary phase, and then drying the separated and treated mixed solution to produce high-purity betulonic acid (purity: more than 99.5%, yield to birch bark: 1.8 wt %).

The step a) may include the steps of: introducing methanol into the reaction product (1) and then filtering the reaction product to remove a blue precipitate ($Cr_2O_3$) and obtain a dark brown filtrate (2); and evaporating 40~50 vol % of the filtrate (2) to recover methanol and acetone (3).

The step b) may include the steps of: introducing ethyl acetate (5) into the concentrated reaction product (4) at a ratio of 1:1.3~2 (v/v) in a liquid-liquid extractor and then stirring the mixture to first extract betulonic acid from an upper ethyl acetate layer (6) in the liquid-liquid extractor; and introducing ethyl acetate (8) into a lower layer (7) of the liquid-liquid extractor at a ratio of 1:1~2 (v/v) to second extract betulonic acid from an upper ethyl acetate layer (9) in another liquid-liquid extractor.

The step c) may include the steps of: introducing a saturated aqueous sodium chloride solution (brine) (12) into the ethyl acetate solution (11), in which betulonic acid is dissolved, at a ratio of 2:1 (v/v) in a liquid-liquid extractor to first separate and remove impurities (14) from an lower layer of the liquid-liquid extractor; and introducing a saturated aqueous sodium chloride solution (brine) (15) into the ethyl acetate solution (13), in which the first washed betulonic acid is dissolved, at a ratio of 3~5:1 (v/v) in another liquid-liquid extractor to secondly separate and remove water-soluble impurities (15) from an lower layer of the liquid-liquid extractor.

The step d) may include the steps of: introducing hexane or petroleum ether, as a nonpolar solvent (18), into the washed ethyl acetate solution at a ratio of 1:1~5 (v/v) to precipitate green impurities, thus removing nonpolar substances; supplying an organic solvent, in which betulonic acid is dissolved, into an adsorption tower filled with at least one polar adsorbent (aluminum oxide or silica gel) to adsorb and remove impurities having higher polarity than betulonic acid, thus removing polar substances; and evaporating and drying the betulonic acid-containing solution having passed through the adsorption tower to produce white crystalline betulonic acid (purity: more than 92%, yield to birch bark: 2.75 wt %).

The step e) may be the step of: dissolving the produced betulonic acid in a mixed solvent of ethanol and acetonitrile (1:1 (v/v)) to obtain a sample, separating and treating the sample while supplying an eluent of acetonitrile and water (86:14 (v/v)) into a semi-preparative chromatography column filled with $C_{18}$ stationary phase at a flow velocity of 0.03~0.1 cm/sec, and then evaporating and drying the separated and treated sample to produce white crystalline betulonic acid (purity: more than 99.5%, yield to birch bark: 1.8 wt %).

Another aspect of the present invention provides a method of preparing a piperazine betulonic acid amide derivative using high-purity betulonic acid, including the steps of: dissolving betulonic acid chloride obtained from the high-purity betulonic acid prepared by the method of any one of claims 1 to 6 in anhydrous dichloromethane ($CH_2Cl_2$); reacting the dissolved betulonic acid chloride with anhydrous triethylamine and any one selected from among 1-(4-fluorophenyl) piperazine, 1-(3,4-dichlorophenyl) piperazine, 1-(4-nitrophenyl)piperazine, 1-(2-pyridyl) piperazine, 1-(2-pyrimidyl) piperazine and 1-(4-trifluoromethylphenyl) piperazine; washing and drying the reaction product; and fractionating the washed and dried reaction product using a reverse-phase $C_{18}$ semi-preparative chromatography column to synthesize a piperazine betulonic acid amide derivative.

The piperazine betulonic acid amide derivative synthesized in the step b) may be any one selected from among 4-(4'-fluorophenylpiperazine-1-yl) amide betulonic acid, 4-(3',4'-dichlorophenylpiperazine-1-yl) amide betulonic acid, 4-(4'-nitrophenylpiperazine-1-yl) amide betulonic acid, 4-(2-pyridylpiperazine-1-yl) amide betulonic acid, 4-(2-pyrimidylpiperazine-1-yl) amide betulonic acid and 4-(4'-trifluoromethylphenylpiperazine-1-yl) amide betulonic acid.

Still another aspect of the present invention provides a piperazine betulonic acid amide derivative using high-purity betulonic acid, the derivative being represented by Chemical Formula 1 below:

<Chemical Formula 1>

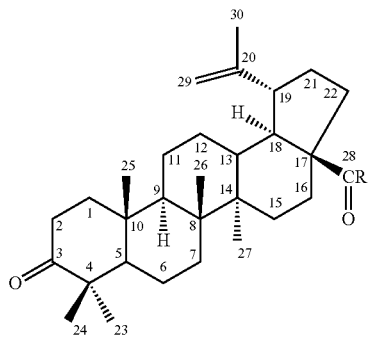

wherein R is any one selected from among 1-(4-fluorophenyl) piperazine, 1-(3,4-dichlorophenyl) piperazine, 1-(4-nitrophenyl)piperazine, 1-(2-pyridyl) piperazine, 1-(2-pyrimidyl) piperazine and 1-(4-trifluoromethylphenyl) piperazine.

Still another aspect of the present invention provides a method of purifying Boc-lysinated betulonic acid using the high-purity betulonic acid obtained by the method as a starting material, including the steps of: a) dissolving an organic synthesis reaction product of a Boc-lysinated betulonic acid monomer ester in a mixed solvent of ethyl acetate and hexane (or petroleum ether) and then treating the resultant solution with an adsorption tower filed with aluminum oxide (or silica gel) to remove polar impurities; b) evaporating and drying the solution discharged from the adsorption tower to obtain white crystals, dissolving the white crystals in ethanol, crystallizing impurities in the resultant solution at 20~–2° C., and then filtering this solution to remove the crystallized impurities; c) evaporating and drying the filtrate to obtain crystals, dissolving the crystals in ethanol, and then fractionating the resultant solution using a reverse phase $C_{18}$ chromatography to obtain a Boc-lysinated betulonic acid monomer ester having a purity of 99% or more (yield to birch bark: 0.58 w %); and (d) dissolving the Boc-lysinated betulonic acid monomer ester in dichloromethane (DCM) or tetrahydrofuran (THF), adding sodium hydroxide (NaOH), lithium hydroxide (LiOH) or potassium hydroxide (KOH) thereto, hydrolyzing the resultant solution, and then fractionating the hydrolysis reaction product using a reverse phase $C_{18}$ chromatography to obtain Boc-lysinated betulonic acid (purity: more than 99.5%. yield to birch bark: 0.47 w %).

In the step a), the mixed solvent may have a mixing ratio of ethylacetate:hexane (or petroleum ether)=1:0.4~2.4 (v/v), and may remove polar impurities contained in the organic synthesis reaction product of a Boc-lysinated betulonic acid monomer ester, the retention time of the polar impurities in the reaction product being 4 minutes or less.

The step b) may include the steps of: dissolving white crystals in ethanol to make a sample having a concentration of 10~16 g/L, leaving the sample at 20~–2° C. to crystallize impurities having a retention time of 15±0.5 minutes, and then filtering the sample to first remove the crystallized impurities; evaporating and drying a filtrate, dissolving the filtrate in ethanol to make a sample having a concentration of 19~30 g/L, leaving the sample at 20~–2° C. to crystallize impurities having a retention time of 15±0.5 minutes, and then filtering the sample to secondly remove the crystallized impurities; and evaporating and drying a filtrate, dissolving the filtrate in ethanol to make a sample having a concentration of 50~85 g/L, leaving the sample at 20~–2° C. to crystallize impurities having a retention time of 15±0.5 minutes, and then filtering the sample to thirdly remove the crystallized impurities.

Advantageous Effects

As described above, the present invention provides an advanced purification technology of producing high-purity betulonic acid (purity: 99.5%, yield to birch bark: 1.8 wt %) from the organic synthesis reaction product of betulin and a Jones oxidation reagent.

Further, the present invention provides a technology of preparing a piperazine betulonic acid amide derivative, which is a betulonic acid derivative having an antibacterial function as a chemical drug, using the high-purity betulonic acid produced by the advanced purification technology.

Further, the present invention provides a technology of purifying a Boc-lysinated betulonic acid monomer ester by removing residual reactants and side-products from the organic synthesis reaction product of lysine and the high-purity betulonic acid (starting material) obtained by the advanced purification technology, and a technology of purifying Boc-lysinated betulonic acid from the hydrolysis reaction product of the high-purity Boc-lysinated betulonic acid monomer ester to produce high-purity betulonic acid (purity: more than 99.5%, yield to birch bark: 0.47 wt %).

Consequently, these technologies can be practically used in methods of producing therapeutic agents for an androgen-dependent prostatic cancer cells (LNCaP) and androgen-independent prostatic cancer cells (PC-3 and DU-145), thus conferring great expectations for industrial applicability.

BEST MODE

The constitutions, functions and advantages of the present invention will be more clearly understood from the following detailed description of preferred embodiments taken in conjunction with the accompanying drawings. Further, in the description of the present invention, when it is determined that the detailed description of the related art would obscure the gist of the present invention, the description thereof will be omitted.

Figure 1A:
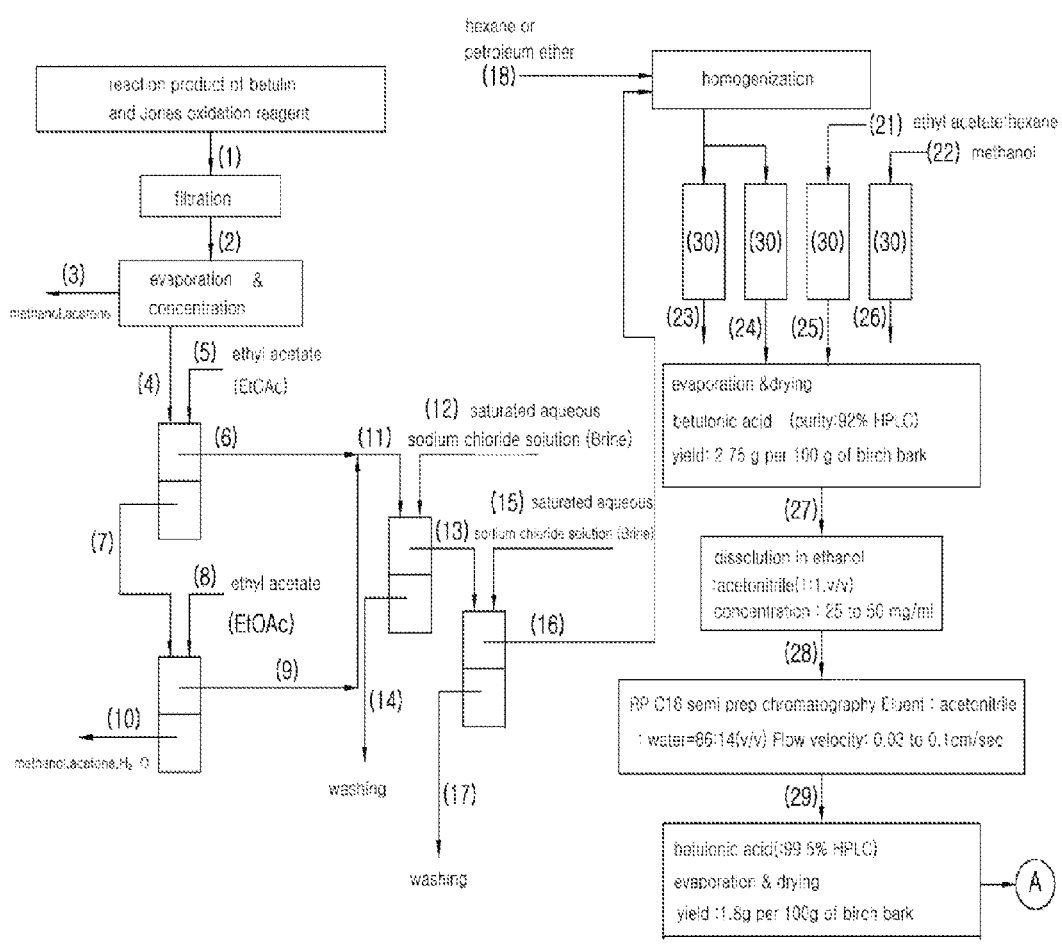
FIG. 1a is a schematic view showing a purification method of producing high-purity betulonic acid according to an embodiment of the present invention.
Figure 1B:
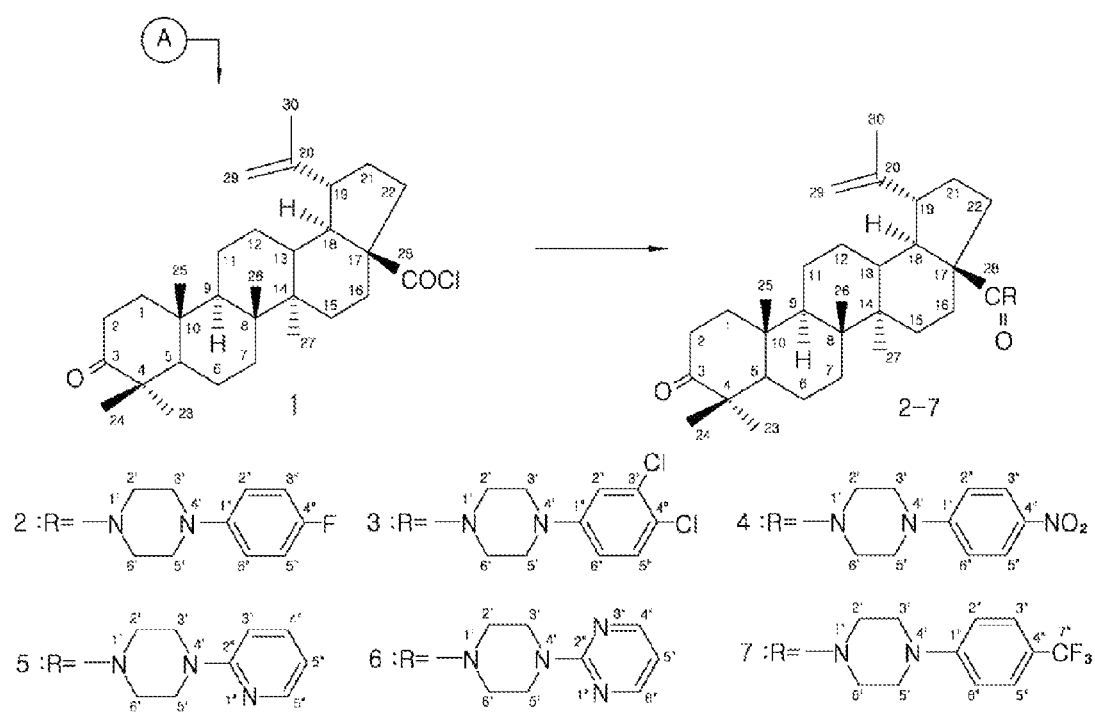
FIG. 1b is a view showing piperazine betulonic acid derivatives using the high-purity betulonic acid.

FIG. 1a is a schematic view showing a purification method of producing high-purity betulonic acid according to an embodiment of the present invention, and FIG. 1b is a view showing piperazine betulonic acid derivatives using the high-purity betulonic acid.

In the purification method of producing high-purity betulonic acid according to the present invention, basically, betulin is dissolved in acetone and then chemically with a Jones oxidation reagent ($CrO_3$/c-$H_2SO_4$/$H_2O$) to convert betulin into betulonic acid, methanol is introduced into the resultant solution to precipitate impurities included in the reaction product, and then betulonic acid is extracted into an organic solvent layer. This organic solvent layer contains $Cr_2O_3$, water, acetone, methanol, unreacted betulin and by-products as well as betulonic acid. Therefore, in order for betulonic acid to be used as a raw material for synthesizing derivatives having biological activity, an advanced purification method of effectively removing unreacted betulin and impurities according to the present invention is required.

Hereinafter, a purification method of producing high-purity betulonic acid according to the present invention will be stepwisely described in detail with reference to FIG. 1.

First, a Jones oxidation reagent ($CrO_3$/c-$H_2SO_4$/$H_2O$) is injected into a mixed solution of acetone and betulin to obtain an organic synthesis reaction product (1).

Subsequently, methanol is introduced into the reaction product (1), and then the reaction product (1) is filtered to remove blue impurities and obtain a dark brown filtrate (2).

Subsequently, 40~50 vol % of the filtrate (2) is evaporated to recover methanol and acetone (3) and obtain a concentrate (4).

Subsequently, ethyl acetate (5) is added to the concentrate (4) in a liquid-liquid extractor at a ratio of concentrate (4): ethyl acetate (5)=1:1.3~2 (v/v), at which layer separation easily occurs, and then the mixture is sufficiently stirred to first extract betulonic acid from an upper ethyl acetate layer (6) of the liquid-liquid extractor.

Subsequently, in order to recover betulonic acid existing in a lower layer (7) of the liquid-liquid extractor, ethyl acetate (8) is mixed with the lower layer (7) in another liquid-liquid extractor at a ratio of lower layer (7):ethyl acetate (8)=1:1~2 (v/v), at which layer separation easily occurs, and then the mixture is sufficiently stirred to secondly extract betulonic acid from an upper ethyl acetate layer (9) of the other liquid-liquid extractor.

A mixed ethyl acetate layer (11) of the ethyl acetate layer (6) containing the first extracted betulonic acid and the ethyl acetate layer (9) containing the second extracted betulonic acid is put into another liquid-liquid extractor at ratio of ethyl acetate (11):saturated aqueous sodium hydroxide solution (brine) (12)=2:1 (v/v), at which catalyst suspended solids such as $Cr_2O_3$ and the like are most easily removed in an organic solvent layer, and then first washed with the saturated aqueous sodium hydroxide solution (brine) (12) to first separate and remove impurities (14) from the lower layer of the liquid-liquid extractor.

Subsequently, the first washed ethyl acetate layer (13), in which betulonic acid is dissolved, is put into another liquid-liquid extractor at ratio of ethyl acetate (13):saturated aqueous sodium hydroxide solution (brine) (15)=2:1 (v/v) at which catalyst suspended solids such as $Cr_2O_3$ and the like are most easily removed in an organic solvent layer, and then second washed with the saturated aqueous sodium hydroxide solution (brine) (15) to second remove water-soluble impurities (17) and separate an upper ethyl acetate layer (16) from the lower layer of the liquid-liquid extractor.

Subsequently, hexane or petroleum ether, as a nonpolar solvent (18), is introduced into the second washed ethyl acetate layer (16) at a ratio of ethyl acetate:hexane or petroleum ether=1:1~5 (v/v), at which the selectivity of impurities and betulonic acid in a polar adsorbent is high, to precipitate green impurities, thus removing nonpolar substances.

Subsequently, an organic solvent (19, 20), in which betulonic acid is dissolved, is supplied into at least one adsorption tower filled with a polar adsorbent (aluminum oxide or silica gel) to adsorb and remove impurities having higher polarity than betulonic acid, thus removing polar substances.

Subsequently, a first solution, which was discharged from one adsorption tower (30), is separately collected in an amount of 5~10 fold of the volume of the adsorption tower 30, and then a second solution, which was washed with a mixed solvent (21) of pure ethyl acetate and hexane (or petroleum ether) to recover betulonic acid existing in the pores of another adsorption tower (30), is mixed with the first solution, and then the mixed solution is completely evaporated and dried to produce white crystalline betulonic acid (purity: more than 92%, yield to birch bark: 2.75 wt %).

Subsequently, the white crystalline betulonic acid is dissolved in a mixed solvent of ethanol and acetonitrile (ethanol: acetonitrile=1:1 (v/v), at a ratio of which solubility of the white crystalline betulonic acid is maximized) while it being not split and pecked, thus making a betulonic acid solution (28) having a concentration of 25~50 mg/L, and then the betulonic acid solution (28) is injected into a semi-preparative chromatography column filled with $C_{18}$ stationary phase at a flow velocity of 0.03~0.1 cm/sec while supplying acetonitrile and water as an eluent into the semi-preparative chromatography column at a flow velocity of 0.03~0.1 cm/sec.

Finally, the betulonic acid solution (29) discharged from the semi-preparative chromatography column is completely evaporated and dried to produce white crystalline betulonic acid (purity: more than 99.5%, yield to birch bark: 1.8 wt %).

Through the above procedures, high-purity betulonic acid is produced.

Further, the present invention provides a method of preparing a betulonic acid derivative having an antibacterial activity using the high-purity betulonic acid. This method includes the following steps. In $1^{st}$ step, betulonic acid reacts with oxalyl chloride to obtain betulonic acid chloride 1 of FIG. 1 as an intermediate material.

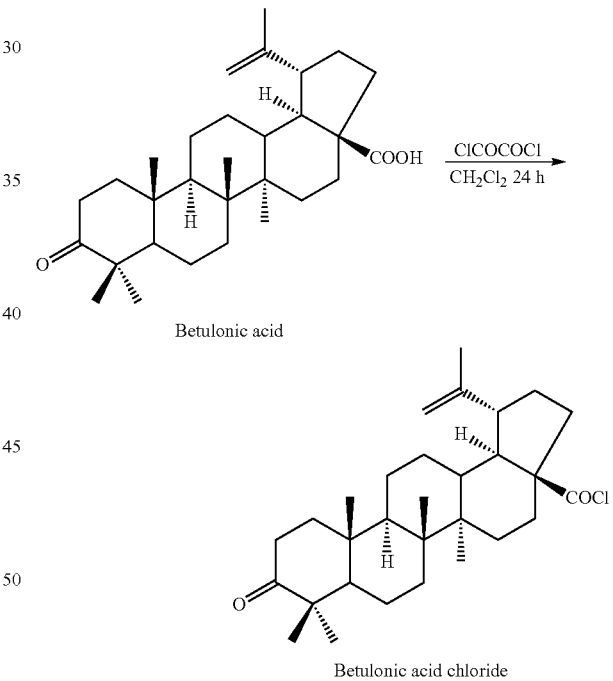

In the $2^{nd}$ step, betulonic acid chloride 1 is dissolved in anhydrous dichloromethane ($CH_2Cl_2$) and then reacts with anhydrous triethylamine and 1-(4-fluorophenyl)piperazine at 15~25° C. at which precipitation does not occur. Then, the reaction product is washed with HCl and $H_2O$, dried with $Na_2SO_4$ and then evaporated to obtain crystals. Then, the crystals are fractionated using a reverse-phase $C_{18}$ semi-preparative chromatography column to obtain 4-(4'-fluorophenylpiperazine-1-yl) amide betulonic acid 2 of FIG. 1.

Or, in the $2^{nd}$ step, betulonic acid chloride 1 is dissolved in anhydrous dichloromethane ($CH_2Cl_2$) and then reacts with anhydrous triethylamine and 1-(3,4-dichlorophenyl) piperazine at 15~25° C. at which precipitation does not occur. Then, the reaction product is washed with HCl and $H_2O$, dried with $Na_2SO_4$ and then evaporated to obtain crystals. Then, the crystals are fractionated using a reverse-phase $C_{18}$ semi-preparative chromatography column to obtain 4-(3',4'-dichlorophenylpiperazine-1-yl) amide betulonic acid 3 of FIG. 1.

Or, in the $2^{nd}$ step, betulonic acid chloride 1 is dissolved in anhydrous dichloromethane ($CH_2Cl_2$) and then reacts with anhydrous triethylamine and 1-(4-nitrophenyl)piperazine at 15~25° C. at which precipitation does not occur. Then, the reaction product is washed with HCl and $H_2O$, dried with $Na_2SO_4$ and then evaporated to obtain crystals. Then, the crystals are fractionated using a reverse-phase $C_{18}$ semi-preparative chromatography column to obtain 4-(4'-nitrophenylpiperazine-1-yl) amide betulonic acid 4 of FIG. 1.

Or, in the $2^{nd}$ step, betulonic acid chloride 1 is dissolved in anhydrous dichloromethane ($CH_2Cl_2$) and then reacts with anhydrous triethylamine and 1-(2-pyridyl) piperazine at 15~25° C. at which precipitation does not occur. Then, the reaction product is washed with HCl and $H_2O$, dried with $Na_2SO_4$ and then evaporated to obtain crystals. Then, the crystals are fractionated using a reverse-phase $C_{18}$ semi-preparative chromatography column to obtain 4-(2-pyridyl piperazine-1-yl) amide betulonic acid 5 of FIG. 1.

Or, in the $2^{nd}$ step, betulonic acid chloride 1 is dissolved in anhydrous dichloromethane ($CH_2Cl_2$) and then reacts with anhydrous triethylamine and 1-(2-pyrimidyl)piperazine at 15~25° C. at which precipitation does not occur. Then, the reaction product is washed with HCl and $H_2O$, dried with $Na_2SO_4$ and then evaporated to obtain crystals. Then, the crystals are fractionated using a reverse-phase $C_{18}$ semi-preparative chromatography column to obtain 4-(2-pyrimidyl piperazine-1-yl) amide betulonic acid 6 of FIG. 1.

Or, in the $2^{nd}$ step, betulonic acid chloride 1 is dissolved in anhydrous dichloromethane ($CH_2Cl_2$) and then reacts with anhydrous triethylamine and 1-(4-trifluoromethylphenyl)piperazine at 15~25° C. at which precipitation does not occur. Then, the reaction product is washed with HCl and $H_2O$, dried with $Na_2SO_4$ and then evaporated to obtain crystals. Then, the crystals are fractionated using a reverse-phase $C_{18}$ semi-preparative chromatography column to obtain 4-(4'-trifluoromethylphenylpiperazine-1-yl) amide betulonic acid 7 of FIG. 1.

Further, the present invention provides a purification method of preparing high-purity Boc-lysinated betulonic acid monomer ester by removing residual reactants and by-products from the organic synthesis reaction product of the obtained high-purity betulonic acid, and a method of producing high-purity Boc-lysinated betulonic acid from the hydrolysis reaction product of the prepared high-purity Boc-lysinated betulonic acid monomer ester. Hereinafter, these methods will be described in detail.

The organic synthesis of Boc-lysinated betuloni acid is disclosed in the documents Kobayashi et al., J. Org. Chem. 66:6626-6623(2001), Zhao et al., J. Org. Chem. 69:270-279 (2004), and Saxena et al., US2006/0154903 A1. The organic synthesis of Boc-lysinated betuloni acid includes the following steps.

In the $1^{st}$ step, the high-purity betulonic acid obtained the method of the present invention reacts with lysine(Boc-Lys(Cbz)-OH) whose primary amine group and secondary amine group are protected by benzyloxycarbonyl(Cbz) and butyloxycarbonyl(Boc) to obtain Boc-Lys(Cbz)-OMe, which is a methyl ester.

In the $2^{nd}$ step, the Cbz(bezoyloxycarbonyl) protecting the primary amine group of the obtained lysine(Boc-Lys(Cbz)-OH) is detached from the Boc-Lys(Cbz)-OMe to obtain Boc-Lys-OMe.

In the $3^{rd}$ step, the obtained Boc-Lys-OMe is bonded to a carboxyl group (—COOH) of betulonic acid C-28 to synthesize Boc-lysinated-betulonic acid monomer ester (Boc-Lys-BOMe).

Figure 3:
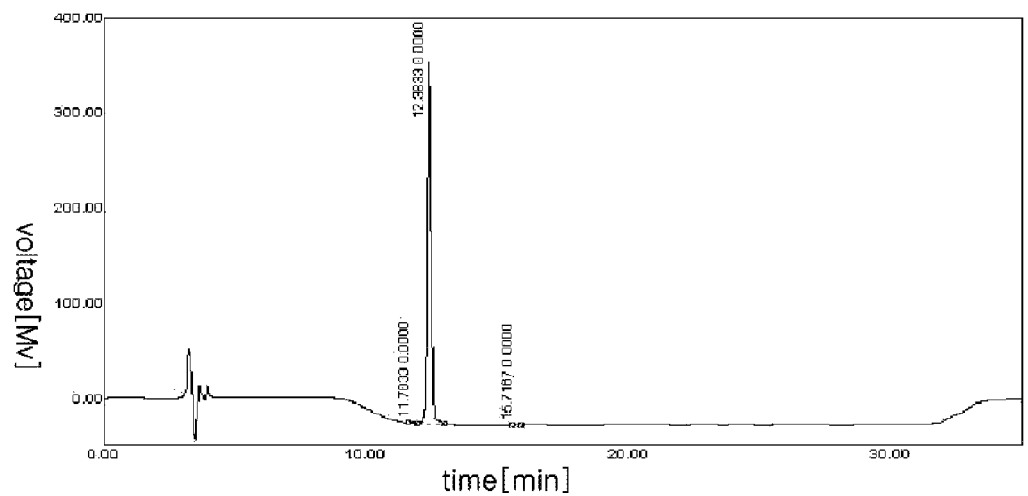
FIG. 3 is graph of HPLC analysis of the organic synthesis reaction product of a Boc-lysinated betulonic acid monomer ester (Boc-Lys-BOA monomer ester) according to an embodiment of the present invention.

In this case, Boc-Lys-BOMe is synthesized by activating the carboxyl group (—COOH) of betulonic acid C-28 in $CH_2Cl_2$ or tetrahydrofuran using 1-hydroxybezotriazole hydrate(HOBt) and 1,3-dicyclohexyl carbodiimide (DCC) catalysts and then bonding the activated carboxyl group (—COOH) thereof to Boc-Lys-OMe. Here, the synthesized Boc-Lys-BOMe contains various impurities such as Boc-Lys-BOMe, HOBt, DCC, unreacted Boc-Lys(Cbz)-OH, etc. FIG. 3 shows the results of analysis of such an organic synthesis reaction product using HPLC (Nova-Pak $C_{18}$ 4 μm, 3.9×300 mm, UV/VIS @ 212 nm) under the gradient elution conditions given in Table 1 below.

TABLE 1

Conditions of HPLC analysis of organic synthesis reaction product of Boc-lysinated betulonic acid monomer ester
HPLC column: Nova-Pak $C_{18}$ 4 μm, 3.9 × 300 mm
Detector: UV/VIS @ 212 nm

| Time (min) | Flow velocity (mL/min) | Eluent A (MeCM, 0.05% TFA) | Eluent B ($H_2O$, 0.05% TFA) |
|---|---|---|---|
| 0~4 | 0.6 | 86 | 14 |
| 4~6 | 0.6 | 86 → 98 | 14 → 2 |
| 6~26 | 0.6 | 98 | 2 |
| 26~28 | 0.6 | 98 → 86 | 2 → 14 |
| 28~ | 0.6 | 86 | 14 |

From FIG. 3, it can be seen that the organic synthesis reaction product includes, based on an area ratio: 50.39% and 3.1% of unconfirmed components having their respective retention times of 3.5 min and 4.1 min; 7.85% of Boc-lysinated betulonic acid monomer ester (Boc-Lys-OMe); and 32.68%, 2.97% and 2.31% of components having their respective retention times of 15.15 min, 16.08 min and 23.23 min. The organic synthesis reaction product is purified to obtain high-purity Boc-Lys-OMe, and this high-purity Boc-Lys-OMe can be used to produce Boc-lysinated betulonic acid. For this purpose, advanced technologies of purifying the organic synthesis reaction product are required.

Hereinafter, the purification method according to the present invention will be described in more detail with reference to FIG. 2.

Figure 2A:
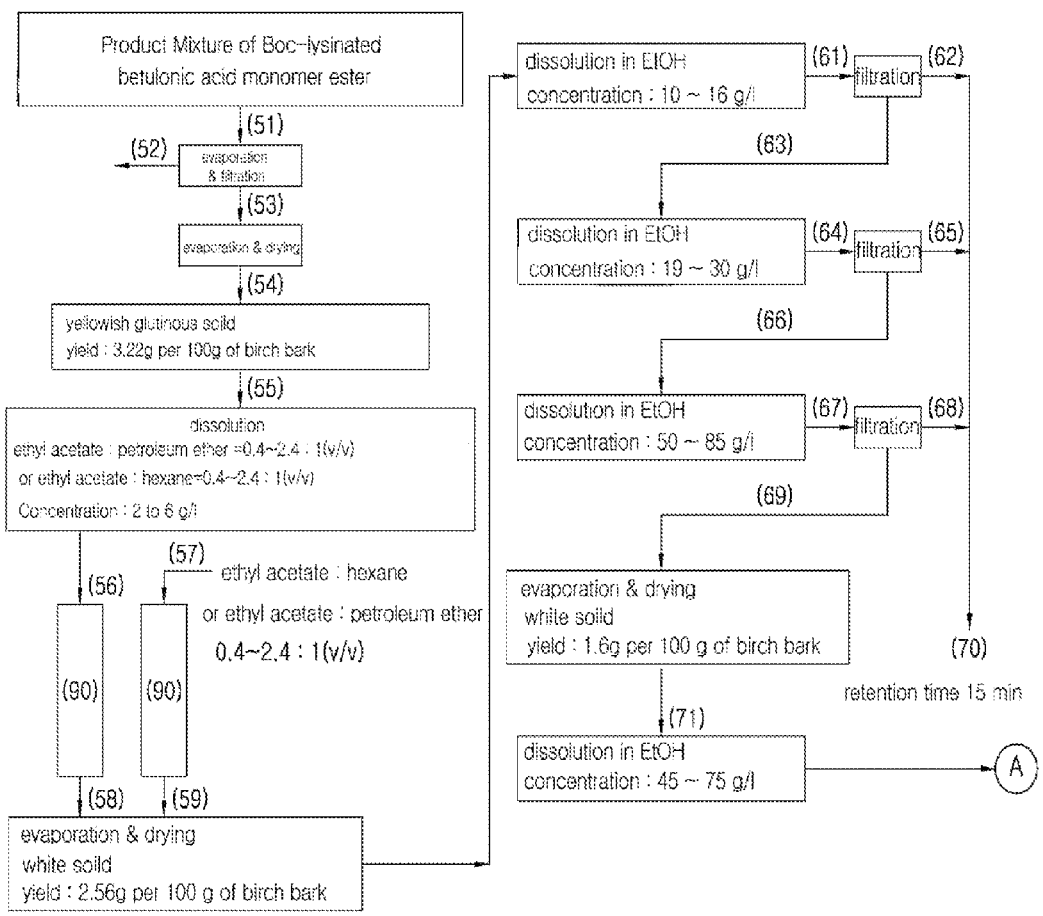
FIG. 2a is a schematic view showing a process of purifying a Boc-lysinated betulonic acid monomer ester from the organic synthesis reaction product of lysine and the high-purity betulonic acid according to an embodiment of the present invention.
Figure 2B:
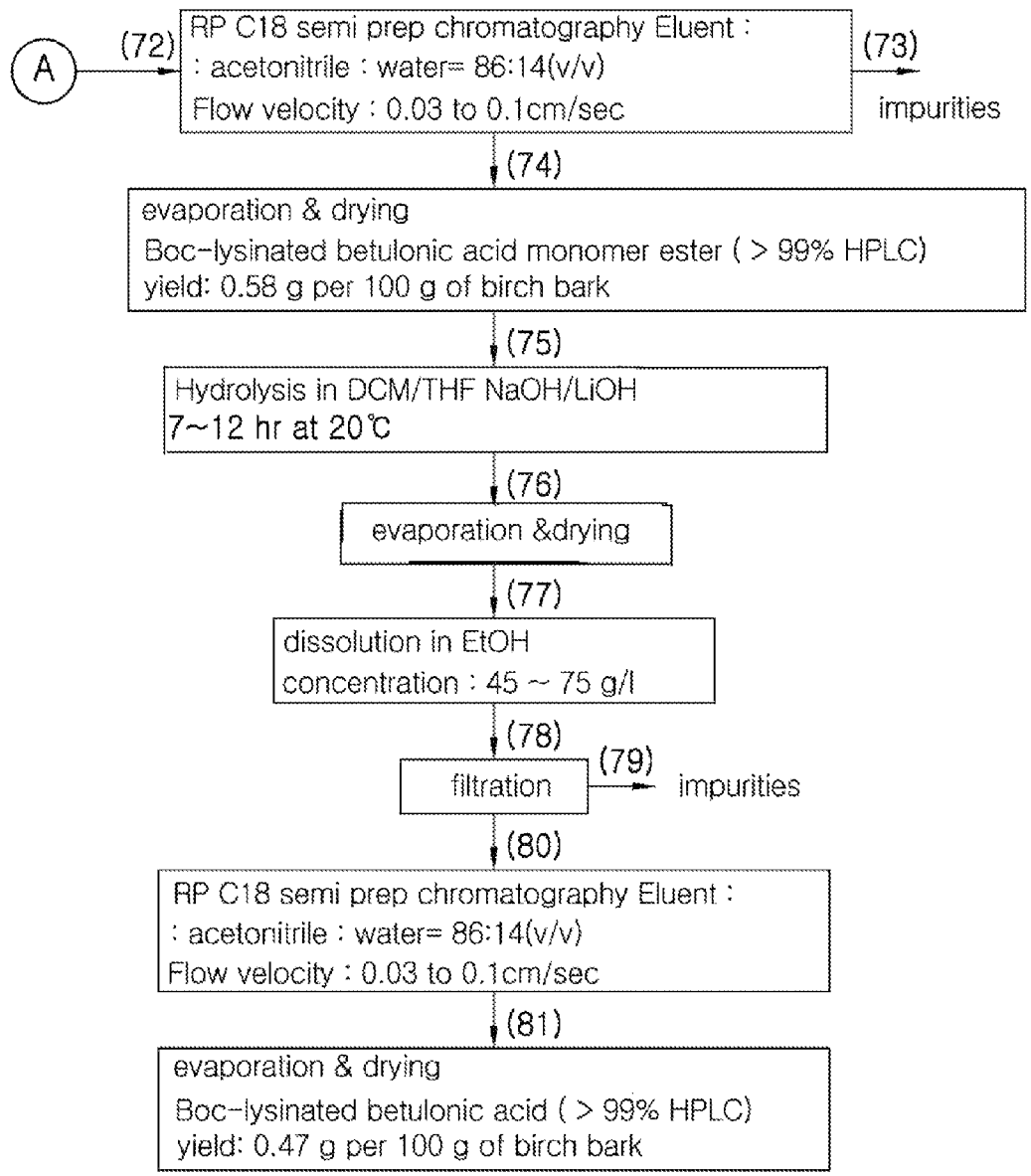
FIG. 2b is a schematic view showing a process of purifying Boc-lysinated betulonic acid from the hydrolysis reaction product of the high-purity Boc-lysinated betulonic acid monomer ester according to an embodiment of the present invention.

FIG. 2a is a schematic view showing a process of purifying a Boc-lysinated betulonic acid monomer ester contained in the reaction product of organic synthesis of lysine and the high-purity betulonic acid according to an embodiment of the present invention, and FIG. 2b is a schematic view showing a process of purifying Boc-lysinated betulonic acid contained in the reaction product of hydrolysis of the high-purity Boc-lysinated betulonic acid monomer ester according to an embodiment of the present invention.

As shown in FIG. 2, the solvent of the organic synthesis reaction product (51) of Boc-lysinated betulonic acid monomer ester is partially evaporated and then filtered to remove white impurities having a retention time of 3.5~4.1 min of FIG. 3. Then, tetrahydrofuran and the like included in the filtrate (53) are evaporated and thus removed to obtain yellow solids (54). Then, these yellow solids (54) are dissolved in a mixed solvent of ethyl acetate and hexane (or petroleum ether) (ratio of ethyl acetate:hexane (or petroleum ether)=1: 0.4~2.4 (v/v), at which the selectivity of yellow solids to a polar adsorbent is high at the time of adsorbing and removing yellow solids using the polar adsorbent) to obtain a sample.

Then, the sample is supplied into an adsorption tower (90) filled with aluminum oxide (or silica gel) to adsorb and remove polar impurities having a retention time of 3.5~4.1 min.

A solution (58) directly discharged from the adsorption tower (90) is mixed with a solution (59) discharged from another adsorption tower (90) after being washed with the mixed solvent of ethyl acetate and hexane (or petroleum ether) (ratio of ethyl acetate:hexane (or petroleum ether)=1: 0.4~2.4 (v/v)), and then this mixed solution is evaporated and dried to obtain white crystals 60.

Subsequently, the white crystals (60) are dissolved in ethanol (EtOH) to make a sample having a concentration of 10~16 g/L which experimentally approximates saturated solubility, and then the sample is left at 20~−2° C. to crystallize impurities having a retention time of 15 min (error range±0.5 minutes, which is changed within this range depending on the degree of contamination of a column, the lifespan of a column, the purity of an eluent or the like even if analysis conditions are accurate), and then filtered to first remove the crystallized impurities (62). Subsequently, the filtrate (63) is evaporated and dried again and then dissolved in ethanol (EtOH) to make another sample (64) having a concentration of 19~30 g/L, and then the sample is left at 20~−2° C. to crystallize impurities having a retention time of 15±0.5 minutes, and then the sample is filtered to secondly remove the crystallized impurities (65). Finally, the filtrate (66) is evaporated and dried and then dissolved in ethanol (EtOH) to make another sample having a concentration of 50~85 g/L, and then the sample is left at 20~−2° C. to crystallize impurities having a retention time of 15±0.5 minutes, and then the sample is filtered to thirdly remove the crystallized impurities (68).

The filtrate (69) is completely evaporated and dried and then dissolved in ethanol (EtOH) or a mixed solvent of acetonitrile and water ($H_2O$) to obtain another sample (72), and then this sample (72) is injected into a reverse phase $C_{18}$ chromatography column. Then, a solution containing Boc-lysinated betulonic acid monomer ester, discharged from the reverse phase $C_{18}$ chromatography column, is separately collected and then evaporated to obtain white crystals (74) having a purity of 99% or more (purity of Boc-lysinated betulonic acid monomer ester: more than 99%, yield to birch bark: 0.58 w %).

Finally, the white crystals (74) are dissolved in dichloromethane (DCM) or tetrahydrofuran (THF), and then the resultant solution is hydrolyzed by the addition of sodium hydroxide (NaOH), lithium hydroxide (LiOH) or potassium hydroxide (KOH) to detach a methyl group, and then the hydrolysis reaction product is fractionated using a reverse phase $C_{18}$ chromatography to obtain Boc-lysinated betulonic acid (purity: more than 99.5%, yield to birch bark: 0.47 w %).

MODE FOR INVENTION

Hereinafter, the present invention will be described in more detail with reference to the following Examples.

Example 1

45 g of betulin and 1100 mL of acetone were put into a reactor, and then uniformly stirred at 10° C. A Jones oxidation reagent ($CrO_3$ 97 g, 310 mL, c-$H_2SO_4$ 65 mL) was put into a funnel, and then introduced into the reactor filled with betulin and acetone through the funnel over 60 min.

Subsequently, the temperature of the reactor was maintained at 25° C., and the mixed solution was stirred for 1 hour to convert betulin into betulonic acid, and then 1000 mL of methanol was put into the reactor. Thus, an organic synthesis reaction was conducted. The subsequent procedures were conducted as follows according to the purification method of FIG. 1.

The organic synthesis reaction product (1) was passed through a glass frit filter to remove blue impurities ($Cr_2O_3$) and obtain 2000 mL of a filtrate (pH 3) (2).

Acetone and methanol (3) were evaporated by a vacuum evaporator to concentrate the filtrate (2) in an amount of 1300 mL.

1300 mL of the concentrated filtrate (4) was mixed with 1800 mL of ethyl acetate (5), and then the mixture was sufficiently stirred and then left until layer separation occurred.

The resulting mixture was separated into 2500 mL of an upper ethyl acetate (EtOAc) layer (6) and 600 mL of a lower layer (7) containing methanol, acetone and water.

600 mL of the lower layer (7) was mixed with 500 mL of ethyl acetate to form another upper ethyl acetate layer (9), and then betulonic acid was separated from the upper ethyl acetate layer (9) and mixed with the first ethyl acetate extract to obtain 3350 mL of an ethyl acetate solution. The ethyl acetate solution was first washed with 1750 mL of a saturated aqueous sodium hydroxide solution (brine) (12) to extract residual impurities (14) and polar substances.

2850 mL of the upper ethyl acetate layer (13) was secondly washed with 850 mL of a saturated aqueous sodium hydroxide solution (brine) (15), and 3200 mL of the upper ethyl acetate solution containing betulonic acid as a major component is treated by an adsorption tower (30) filled with aluminum oxide.

500 ml of the ethyl acetate extract was mixed with 1500 ml of hexane (18) at a ratio of EtOAc:hexane=1:3 to obtain a matrix solution having low polarity, and the matrix solution was supplied into an adsorption tower (30) filled with 170 g of aluminum oxide at a flow velocity of 5 mL/min, and simultaneously 7.45 BV (1 BV=volume of adsorption tower) of an initial solution (23) discharged from the adsorption tower was discarded, and 7.5 BV of a subsequent solution discharged therefrom was collected and then completely evaporated and dried to 2.715 g of white crystals (betulonic acid: 91.99% HPLC, yield to birch bark: 2.45 wt %).

Thereafter, 1.2 BV of a mixed solvent (21) of EtOAc: hexane=1:3 (v/v) is supplied to a semi-preparative chromatography column at a flow velocity of 5 mL/min to recover betulonic acid existing in the pores of the adsorption tower.

The solution (25) discharged from the semi-preparative chromatography column during the washing procedure was completely evaporated and dried to obtain 0.308 g of white crystals (betulonic acid: 87.43%, yield to birch bark: 0.278 wt %).

5 to 9 ml of a matrix solution (25 g/L) prepared by dissolving 1 g of white betulonic acid crystals in 20 mL of ethanol and 20 mL of acetonitrile was introduced into a RP $C_{18}$ semi-preparative chromatography column. Then, a betulonic acid fraction was collected from the column while observing signals detected by UV of 212 nm, and then evaporated and dried to obtain 0.6674 g of white betulonic acid crystals (29) having a purity of 99.69~99.10% (yield to birch bark: 1.8 wt %).

Or, a matrix solution (50 g/L) prepared by dissolving 2 g of the white betulonic acid crystals purified with the column filled with aluminum oxide in 20 mL of ethanol and 20 mL of acetonitrile was purified by RP $C_{18}$ semi-preparative chromatography column to obtain 1.0864 g of white betulonic acid crystals (29) having a purity of 96.54~97.29 (yield to birch bark: 1.43 wt %).

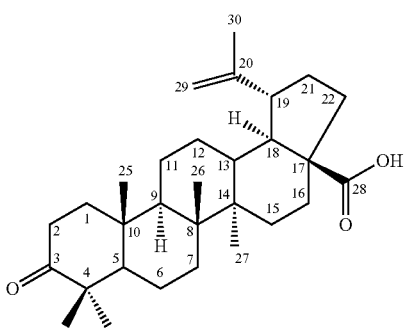

Betulonic acid $^1$H NMR (600 MHz, C$_5$D$_5$N):

δ=4.74 (1H, s, H-29a), 4.62 (1H, s, H-29b), 3.03 (2H, m, H-2), 1.70 (3H, s, H-30), 1.44 (3H, s, H-27), 1.07 (3H, s, H-26), 1.04 (3H, s, H-23), 1.05 (3H, s, H-27), 0.99, 0.98 (3H, s, H-25), 0.93 (3H, s, H-25)

$^{13}$C NMR (125 MHz, C$_5$D$_5$H):

δ=218.55 (C3), 182.80 (C28), 150.52 (C20), 109.98 (C29), 56.62 (C17), 55.62 (C5), 50.03 (C9), 49.36 (C18), 47.54 (C4), 47.10 (C19), 42.68 (C14), 40.82 (C8), 39.80 (C1), 38.71 (C13), 37.25 (C10), 37.11 (C22), 34.33 (C2), 33.78 (C7), 32.31 (C16), 30.75 (C15), 29.88 (C21), 26.84 (C23), 25.67 (C12), 21.56 (C11), 21.20 (C24), 19.82 (C6), 19.57 (C30), 16.17 (C25), 16.02 (C26), 14.83 (C27).

Example 2

0.55 g (1.16 mmol) of betulonic acid chloride was dissolved in 35 mL of anhydrous dichloromethane (CH$_2$Cl$_2$), and then 0.65 mL (4.64 mmol) of anhydrous triethylamine and 0.42 g (2.32 mmol) of 1-(4-fluorophenyl) piperazine were added thereto, and then stirred at 25° C. for 48 hours.

The resulting product was washed with 10% HCl (40 mL×3), further washed with pure water (40 mL×3), and then dried by 10 g of anhydrous Na$_2$SO$_4$ to remove a solvent therefrom.

Dichloromethane (DCM) was evaporated from the washed and dried product to obtain 0.72 g of light brown solids, these light brown solids were dissolved in ethanol to prepare a sample, and then this sample was introduced into RP C$_{18}$ semi-preparative chromatography column to separate a 4-(4'-fluorophenylpiperazine-1-yl) amide betulonic acid fraction. Then, this fraction was evaporated and dried to obtain 0.63 g of 4-(4'-fluorophenylpiperazine-1-yl) amide betulonic acid (yield: 89.8%).

C$_{40}$H$_{57}$FN$_2$O$_2$ 4-(4'-fluorophenylpiperazine-1-yl) amide betulonic acid 2

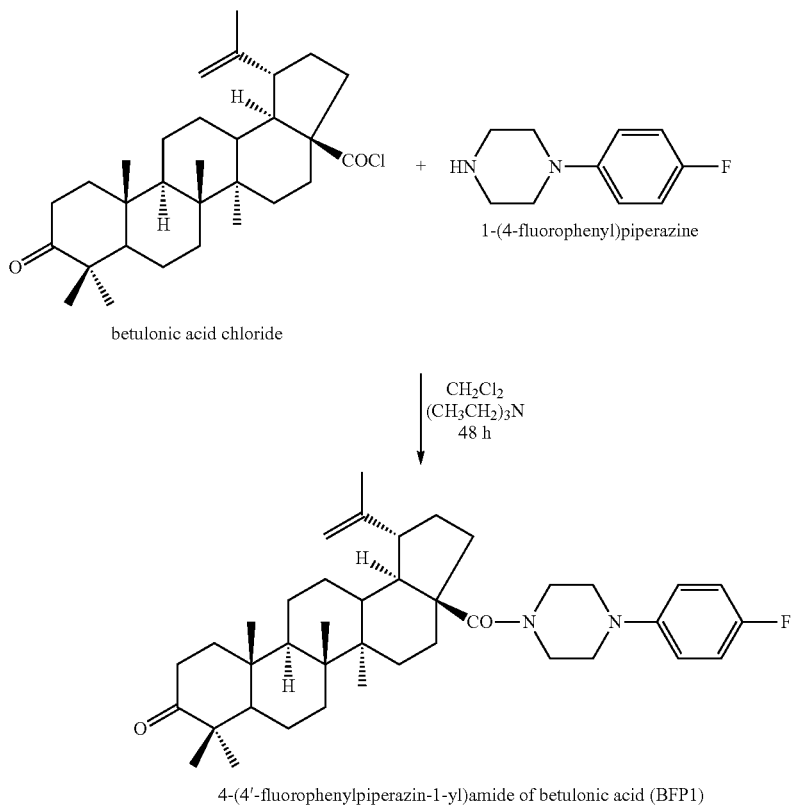

$^1$H NMR (600 MHz, CDCl$_3$):

A white crystalline solid, m.p. 151-152° C. IR (ATR) u$_{max}$ cm$^{-1}$: 2941, 1702 (C=O), 1634 (CONH), 1508, 1409, 1227, 1189, 1025, 880, 820. $^1$H NMR (600 MHz, CDCl$_3$): δ 0.93 (3H, s, Me-25), 0.94 (1H, m, H-12), 1.02 (6H, s, Me-26, 27), 1.03 (3H, s, Me-24), 1.06 (3H, s, Me-23), 1.25-1.48 (13H, m, H-1, 5, 6, 6, 7, 7, 9, 11, 11, 15, 16, 21, 22), 1.19 (1H, m, H-15), 1.58 (1H, m, H-12), 1.59 (1H, t, J=11.4 Hz, H-18), 1.68 (3H, s, Me-30), 1.74 (1H, m, H-22), 1.89 (2H, m, H-1, 21), 2.16 (1H, m, H-16), 2.39 (1H, m, H-2), 2.49 (1H, m, H-2), 2.98

(6H, m, H-13, 19, 3', 3', 5', 5'), 3.76 (4H, m, H-2', 2', 6', 6'), 4.74 and 4.57 (2H, both br. s, H-29), 6.89 (2H, m, H-2", 6"), 6.98 (2H, m, H-3", 5").

Example 3

0.68 g (1.44 mmol) of betulonic acid chloride was dissolved in 35 mL of anhydrous dichloromethane (CH$_2$Cl$_2$), and then 0.8 mL (5.76 mmol) of anhydrous triethylamine and 0.67 g (2.88 mmol) of 1-(3,4-dichlorophenyl) piperazine were added thereto, and then stirred at 25° C. for 48 hours. The resulting product was washed with 10% HCl (40 mL×3), further washed with pure water (40 mL×3), and then a solvent layer was dried by 10 g of anhydrous Na$_2$SO$_4$. A dichloromethane (DCM) layer was evaporated and dried to obtain 0.97 g of light brown solids. These light brown solids were dissolved in ethanol to prepare a sample, and then this sample was fractionated by RP C$_{18}$ semi-prep HPLC, and then completely evaporated and dried to obtain 0.83 g (yield: 86.7%) of 4-(3',4'-dichlorophenylpiperazine-1-yl) amide betulonic acid.

C$_{40}$H$_{56}$Cl$_2$N$_2$O$_2$, 4-(3',4'-dichlorophenylpiperazine-1-yl) amide betulonic acid 3

Example 4

0.8 g (1.69 mmol) of betulonic acid chloride was dissolved in 35 mL of anhydrous dichloromethane (CH$_2$Cl$_2$), and then 0.94 mL (6.76 mmol) of anhydrous triethylamine and 0.7 g (3.38 mmol) of 1-(4-nitrophenyl)piperazine were added thereto, and then stirred at 25° C. for 48 hours. The resulting product was washed with 10% HCl (40 mL×3), further washed with pure water (40 mL×3), and then a solvent layer was dried by 10 g of anhydrous Na$_2$SO$_4$. A dichloromethane (DCM) layer was evaporated and dried to obtain 1.1 g of light brown solids. These light brown solids were dissolved in ethanol to prepare a sample, and then this sample was fractionated by RP C$_{18}$ semi-prep HPLC, and then completely evaporated and dried to obtain 0.86 g (yield: 78.5%) of 4-(4'-nitrophenylpiperazine-1-yl) amide betulonic acid.

$^1$H NMR (600 MHz, CDCl$_3$):

A light yellow crystalline solid, m.p. 197-198° C. IR (ATR) u$_{max}$ cm$^{-1}$: 2940, 1700 (C=O), 1626 (CONH), 1593, 1501, 1328, 1243, 1190, 1113, 1024, 879, 835. $^1$H NMR (600 MHz,

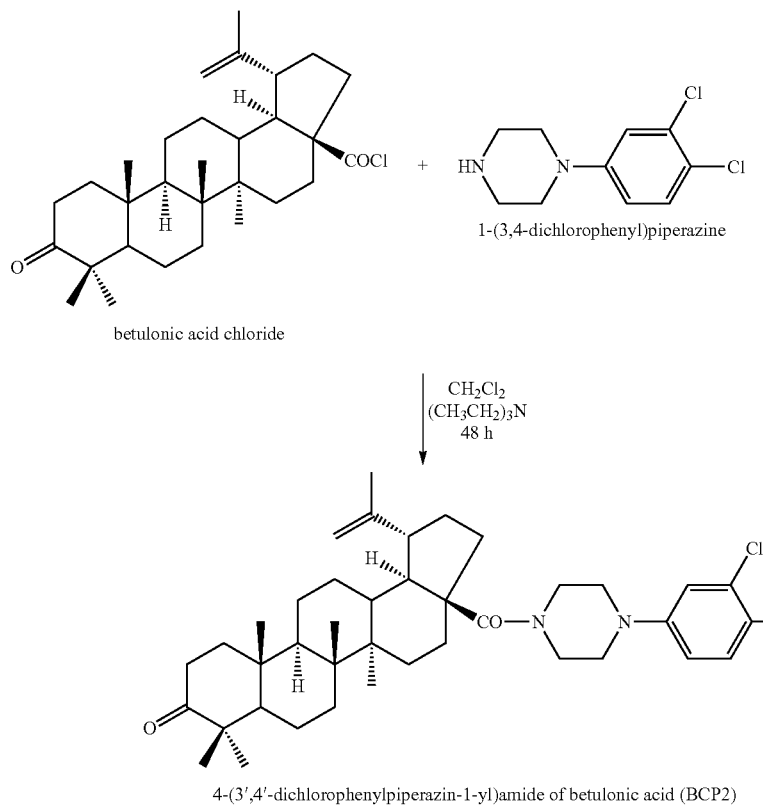

4-(3',4'-dichlorophenylpiperazin-1-yl)amide of betulonic acid (BCP2)

$^1$H NMR (600 MHz, CDCl$_3$):

A white crystalline solid, m.p. 182-183° C. IR (ATR) u$_{max}$ cm$^{-1}$: 2941, 1700 (C=O), 1626 (CONH), 1593, 1483, 1411, 1232, 1192, 1026, 882, 801. $^1$H NMR (600 MHz, CDCl$_2$): δ 0.93 (3H, s, Me-25), 0.94 (1H, m, H-12), 0.97 (6H, s, Me-26, 27), 1.01 (3H, s, Me-24), 1.06 (3H, s, Me-23), 1.19 (1H, m, H-15), 1.30-1.48 (13H, m, H-1, 5, 6, 6, 7, 7, 9, 11, 11, 15, 16, 21, 22), 1.58 (2H, m, H-12, 18), 1.68 (3H, s, Me-30), 1.74 (1H, m, H-22), 1.89 (2H, m, H-1, 21), 2.14 (1H, m, H-16), 2.39 (1H, m, H-2), 2.49 (1H, m, H-2), 2.91 (1H, m, H-13), 2.99 (1H, m, H-19), 3.11 (4H, m, H-3', 3', 5', 5'), 3.76 (4H, m, H-2', 2', 6', 6'), 4.74 and 4.59 (2H, both br. s, H-29), 6.76 (1H, dd, J$_1$=8.4 Hz, J$_2$=2.4 Hz, H-6"), 6.96 (1H, d, J=2.4 Hz, H-5"), 7.29 (1H, m, H-2").

CDCl$_3$): δ 0.93 (3H, s, Me-25), 0.96 (1H, m, H-12), 0.98 (3H, s, Me-27), 0.99 (3H, s, Me-26), 1.03 (3H, s, Me-24), 1.08 (3H, s, Me-23), 1.20 (1H, m, H-15), 1.30-1.52 (14H, m, H-1, 5, 6, 6, 7, 7, 9, 11, 11, 12, 15, 16, 21, 22), 1.61 (1H, t, J=11.4 Hz, H-18), 1.69 (3H, s, Me-30), 1.75 (1H, m, H-22), 1.89 (2H, m, H-1, 21), 2.14 (1H, m, H-16), 2.39 (1H, m, H-2), 2.49 (1H, m, H-2), 2.90 (1H, m, H-13), 3.00 (1H, dt, J$_1$=10.8 Hz, J$_2$=4.2 Hz, H-19), 3.41 (4H, m, H-3', 3', 5', 5'), 3.80 (4H, m, H-2', 2', 6', 6'), 4.74 and 4.60 (2H, both br. s, H-29), 6.85 (2H, d, J=9.6 Hz, H-2", 6"), 8.14 (2H, d, J=9.0 Hz, H-3", 5").

C$_{40}$H$_{57}$N$_3$O$_4$, 4-(4'-nitrophenylpiperazine-1-yl) amide betulonic acid 4

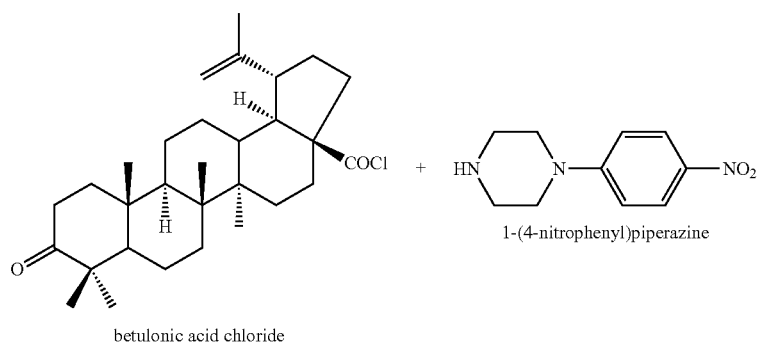

betulonic acid chloride 1-(4-nitrophenyl)piperazine

CH₂Cl₂
(CH₃CH₂)₃N
48 h

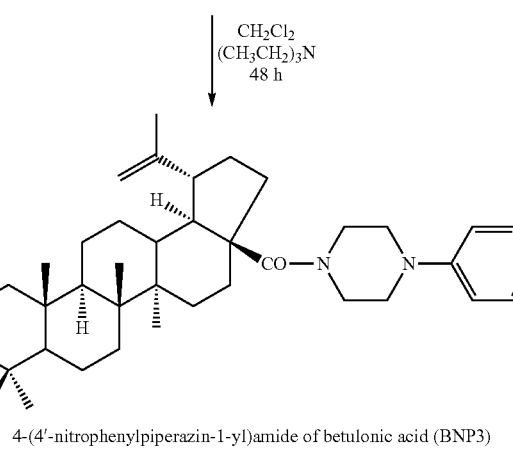

4-(4'-nitrophenylpiperazin-1-yl)amide of betulonic acid (BNP3)

Example 5

0.77 g (1.63 mmol) of betulonic acid chloride was dissolved in 40 mL of anhydrous dichloromethane (CH$_2$Cl$_2$), and then 0.65 mL (6.52 mmol) of anhydrous triethylamine and 0.68 g (3.26 mmol) of 1-(2-pyridyl) piperazine were added thereto, and then stirred at 25° C. for 48 hours. The resulting product was washed with 10% HCl (40 mL×3), further washed with pure water (40 mL×3), and then a solvent layer was dried by 10 g of anhydrous Na$_2$SO$_4$. A dichloromethane (DCM) layer was evaporated and dried to obtain 1.0 g of light brown solids. These light brown solids were dissolved in ethanol to prepare a sample, and then this sample was fractionated by RP C$_{18}$ semi-prep HPLC, and then completely evaporated and dried to obtain 0.85 g (yield: 87.6%) of white crystalline 4-(2-pyridyl piperazine-1-yl)amide betulonic acid.

$^1$H NMR (600 MHz, CDCl$_3$):
A white crystalline solid, m.p. 158-159° C. IR (ATR) u$_{max}$ cm$^{-1}$: 2938, 1703 (C=O), 1633 (CONH), 1592, 1478, 1435, 1243, 1189, 1020, 980, 882, 773. $^1$H NMR (600 MHz, CDCl$_3$): δ 0.93 (3H, s, Me-25), 0.95 (1H, m, H-12), 0.98 (6H, s, Me-26, 27), 1.01 (3H, s, Me-24), 1.06 (3H, s, Me-23), 1.19 (1H, m, H-15), 1.30-1.50 (14H, m, H-1, 5, 6, 6, 7, 7, 9, 11, 11, 12, 15, 16, 21, 22), 1.59 (1H, m, H-18), 1.69 (3H, s, Me-30), 1.74 (1H, s, H-22), 1.89 (2H, m, H-1, 21), 2.03 (1H, m, H-16), 2.39 (1H, m, H-2), 2.49 (1H, m, H-2), 2.94 (1H, m, H-13), 3.00 (1H, td, J$_1$=10.8 Hz, J$_2$=3.6 Hz, H-19), 3.51 (4H, m, H-3', 3', 5', 5'), 3.73 (4H, m, H-2', 2', 6', 6'), 4.74 and 4.59 (2H, both br. s, H-29), 6.68 (2H, m, H-3", 5"), 7.52 (1H, m, H-4"), 8.20 (1H, m, H-6").

C$_{39}$H$_{57}$N$_3$O$_2$, 4-(2-pyridyl piperazine-1-yl) amide betulonic acid 5

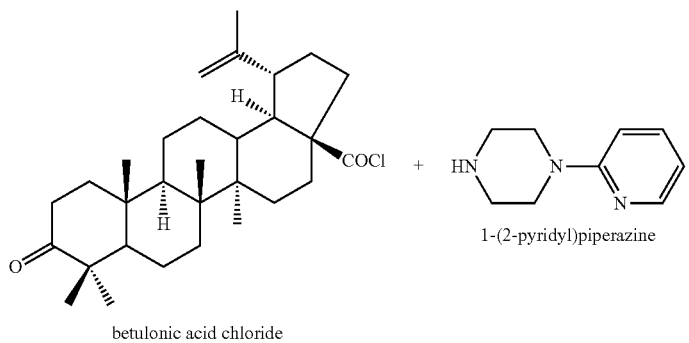

betulonic acid chloride 1-(2-pyridyl)piperazine

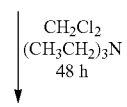

CH₂Cl₂
(CH₃CH₂)₃N
48 h

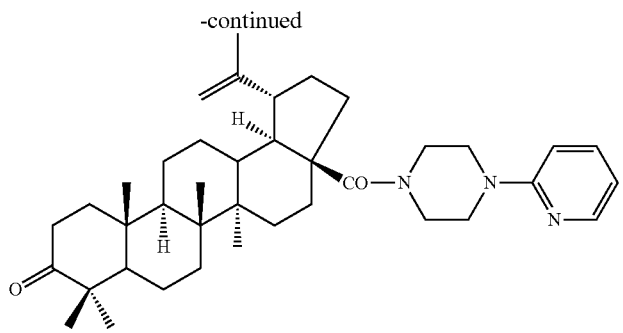

4-(2-pyridyl piperazin-1-yl)amide of betulonic acid (sample BPP4)

Example 6

0.75 g (1.54 mmol) of betulonic acid chloride was dissolved in 40 mL of anhydrous dichloromethane (CH₂Cl₂), and then 0.62 mL (6.16 mmol) of anhydrous triethylamine and 0.52 g (3.08 mmol) of 1-(2-pyrimidyl)piperazine were added thereto, and then stirred at 25° C. for 48 hours. The resulting product was washed with 10% HCl (40 mL×3), further washed with pure water (40 mL×3), and then a solvent layer was dried by 10 g of anhydrous Na₂SO₄. A dichloromethane (DCM) layer was evaporated and dried to obtain 1.05 g of light brown solids. These light brown solids were dissolved in ethanol to prepare a sample, and then this sample was fractionated by RP C$_{18}$ semi-prep HPLC, and then completely evaporated and dried to obtain 0.98 g (yield: 77.8%) of 4-(2-pyrimidyl piperazine-1-yl) amide betulonic acid.

$^1$H NMR (600 MHz, CDCl₃):

A white crystalline solid, m.p. 109-110° C. IR (ATR) u$_{max}$ cm$^{-1}$: 2940, 1703 (C=O), 1633 (CONH), 1584, 1448, 1257, 1188, 982, 879, 797. $^1$H NMR (600 MHz, CDCl₃): δ 0.93 (3H, s, Me-25), 0.95 (1H, m, H-12), 0.98 (6H, s, Me-26, 27), 1.02 (3H, s, Me-24), 1.06 (3H, s, Me-23), 1.20 (1H, m, H-15), 1.30-1.50 (13H, m, H-1, 5, 6, 6, 7, 7, 9, 11, 11, 15, 16, 21, 22), 1.59 (2H, m, H-12, 18), 1.69 (3H, s, Me-30), 1.75 (1H, m, H-22), 1.89 (2H, m, H-1, 21), 2.16 (1H, m, H-16), 2.39 (1H, m, H-2), 2.50 (1H, m, H-2), 2.94 (1H, m, H-13), 3.00 (1H, dt, J₁=10.8 Hz, J₂=3.6 Hz, H-19), 3.69 (4H, m, H-3', 3', 5', 5'), 3.76 (4H, m, H-2', 2', 6', 6'), 4.74 and 4.59 (2H, both br. s, H-29), 6.55 (1H, m, H-5"), 8.33 (2H, m, H-4", 6").

C$_{38}$H$_{56}$N₄O₂, 4-(2-pyrimidyl piperazine-1-yl) amide betulonic acid 6

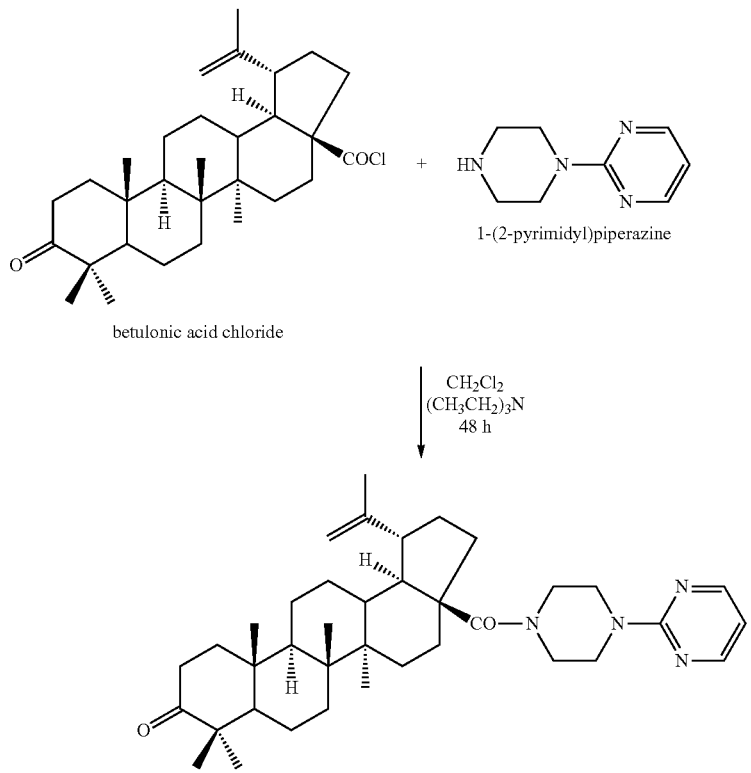

4-(2-pyrimidyl piperazin-1-yl)amide of betulonic acid (sample BPRP5)

Example 7

0.61 g (1.29 mmol) of betulonic acid chloride was dissolved in 40 mL of anhydrous dichloromethane (CH$_2$Cl$_2$), and then 0.72 mL (5.16 mmol) of anhydrous triethylamine and 0.60 g (2.58 mmol) of 1-(4-trifluoromethylphenyl)piperazine were added thereto, and then stirred at 25° C. for 48 hours. The resulting product was washed with 10% HCl (40 mL×3), further washed with pure water (40 mL×3), and then a solvent layer was dried by 10 g of anhydrous Na$_2$SO$_4$. A dichloromethane (DCM) layer was evaporated and dried to obtain 0.85 g of light brown solids. These light brown solids were dissolved in ethanol to prepare a sample, and then this sample was fractionated by RP C$_{18}$ semi-prep HPLC, and then completely evaporated and dried to obtain 0.64 g (yield: 74.9%) of 4-(4'-trifluoromethylphenylpiperazine-1-yl) amide betulonic acid.

$^1$H NMR (600 MHz, CDCl$_3$):
A white crystalline solid, m.p. 229-230° C. IR (ATR) u$_{max}$ cm$^{-1}$: 2944, 1704 (C=O), 1616 (CONH), 1525, 1458, 1332, 1230, 1112, 1073, 1023, 885, 830. $^1$H NMR (600 MHz, CDCl3): 0.93 (3H, s, Me-25), 0.96 (1H, m, H-12), 0.97 (3H, s, Me-27), 0.98 (3H, s, Me-26), 1.02 (3H, s, Me-24), 1.06 (3H, s, Me-23), 1.19 (1H, m, H-15), 1.30-1.52 (12H, m, H-1, 5, 6, 6, 7, 7, 9, 11, 11, 15, 16, 21), 1.59 (2H, m, H-12, 18), 1.69 (3H, s, Me-30), 1.75 (1H, m, H-22), 1.89 (2H, m, H-1, 21), 2.01 (1H, m, H-22), 2.16 (1H, m, H-16), 2.39 (1H, m, H-2), 2.49 (1H, m, H-2), 2.92 (1H, m, H-13), 3.00 (1H, dt, J$_1$=11.4 Hz, J$_2$=4.2 Hz, H-19), 3.41 (4H, m, H-3', 3', 5', 5'), 3.78 (4H, m, H-2', 2', 6', 6'), 4.74 and 4.60 (2H, both br. s, H-29), 6.94 (2H, d, J=8.4 Hz, H-2", 6"), 7.51 (2H, d, J=8.4 Hz, H-3", 5").

C$_{41}$H$_{59}$N$_2$O$_2$F$_3$, 4-(4'-trifluoromethylphenylpiperazine-1-yl) amide betulonic acid 7

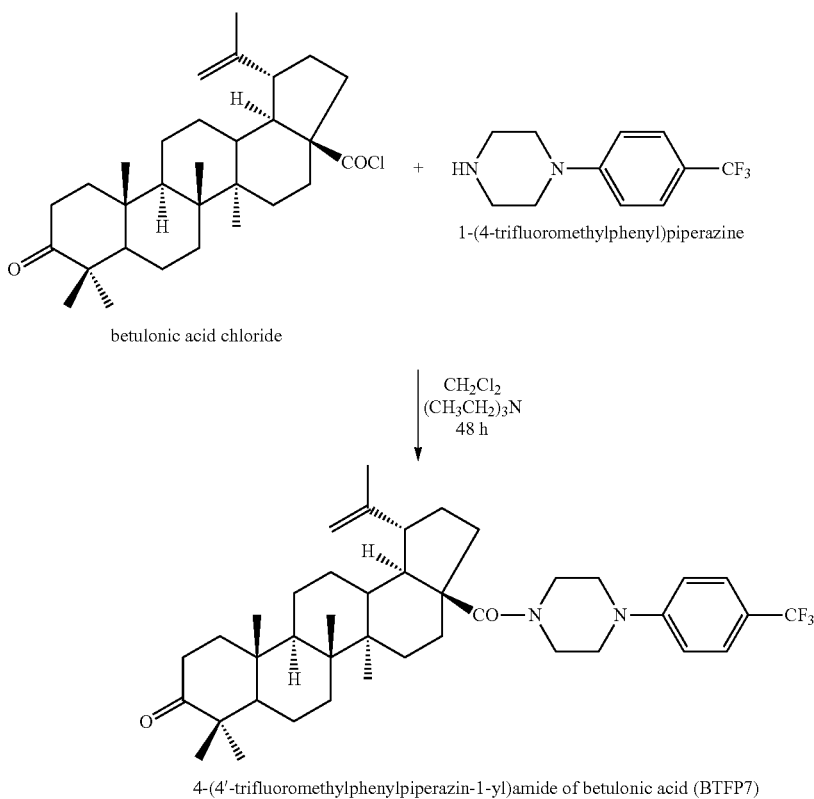

betulonic acid chloride 1-(4-trifluoromethylphenyl)piperazine

CH$_2$Cl$_2$
(CH$_3$CH$_2$)$_3$N
48 h 4-(4'-trifluoromethylphenylpiperazin-1-yl)amide of betulonic acid (BTFP7)

$^{13}$C and $^1$H NMR spectra (respectively, 125 and 600 MHz) of samples dissolved in CDCl$_3$ were analyzed using a Varian UNITY INOVA 600 spectrometer, and thus the chemical shifts of the samples were evaluated by calculating the δ (ppm) values of the samples to tetramethylsilane (TMS), and the molecular structures of the samples were observed by $^{13}$C NMR, as given in Table 2 below.

TABLE 2

$^{13}$C NMR spectral data of BOA, BOCl and six synthesized compounds (125 MHz, CDCl$_3$)

| C atom | [도1]의 1 | [도1]의 2 | [도1]의 3 | [도1]의 4 | [도1]의 5 | [도1]의 6 | [도1]의 7 |
|---|---|---|---|---|---|---|---|
| C-1 | 39.84 | 39.89 | 39.88 | 39.88 | 39.88 | 39.87 | 39.89 |
| C-2 | 34.31 | 34.39 | 34.38 | 34.36 | 34.37 | 34.37 | 34.39 |
| C-3 | 218.32 | 218.50 | 218.50 | 218.42 | 218.47 | 218.45 | 218.54 |

TABLE 2-continued $^{13}$C NMR spectral data of BOA, BOCl and six synthesized compounds (125 MHz, CDCl$_3$)

| C atom | [도1]의 1 | [도1]의 2 | [도1]의 3 | [도1]의 4 | [도1]의 5 | [도1]의 6 | [도1]의 7 |
|---|---|---|---|---|---|---|---|
| C-4 | 47.55 | 47.57 | 47.57 | 47.56 | 47.55 | 47.54 | 47.58 |
| C-5 | 55.19 | 55.27 | 55.26 | 55.25 | 55.26 | 55.26 | 55.26 |
| C-6 | 19.80 | 19.84 | 19.83 | 19.83 | 19.84 | 19.83 | 19.83 |
| C-7 | 33.76 | 33.88 | 33.87 | 33.88 | 33.88 | 33.87 | 33.87 |
| C-8 | 40.86 | 40.81 | 40.81 | 40.81 | 40.81 | 40.80 | 40.81 |
| C-9 | 50.13 | 50.41 | 50.40 | 50.38 | 50.41 | 50.40 | 50.40 |
| C-10 | 37.11 | 37.15 | 37.15 | 37.14 | 37.14 | 37.14 | 37.15 |
| C-11 | 21.57 | 21.87 | 21.86 | 21.85 | 21.87 | 21.87 | 21.86 |
| C-12 | 25.54 | 25.85 | 25.83 | 25.82 | 25.86 | 25.85 | 25.83 |
| C-13 | 37.98 | 37.19 | 37.19 | 37.21 | 37.19 | 37.19 | 37.19 |
| C-14 | 42.69 | 42.16 | 42.16 | 42.18 | 42.16 | 42.16 | 42.17 |
| C-15 | 29.76 | 30.01 | 30.01 | 30.03 | 30.01 | 30.01 | 30.01 |
| C-16 | 32.37 | 33.88 | 33.87 | 33.88 | 33.88 | 33.87 | 33.87 |
| C-17 | 67.96 | 54.76 | 54.76 | 54.80 | 54.80 | 54.82 | 54.77 |
| C-18 | 49.79 | 52.78 | 52.75 | 52.73 | 52.80 | 52.81 | 52.74 |
| C-19 | 46.16 | 45.83 | 45.82 | 45.83 | 45.85 | 45.84 | 45.84 |
| C-20 | 149.43 | 151.41 | 151.32 | 151.19 | 151.42 | 151.41 | 151.34 |
| C-21 | 30.02 | 31.50 | 31.48 | 31.46 | 31.50 | 31.50 | 31.47 |
| C-22 | 36.37 | 36.19 | 36.18 | 36.17 | 36.21 | 36.22 | 36.20 |
| C-23 | 26.78 | 26.79 | 26.79 | 26.79 | 26.79 | 26.78 | 26.78 |
| C-24 | 21.23 | 21.24 | 21.24 | 21.22 | 21.22 | 21.22 | 21.24 |
| C-25 | 16.18 | 16.23 | 16.22 | 16.21 | 16.21 | 16.24 | 16.23 |
| C-26 | 15.92 | 16.13 | 16.12 | 16.12 | 16.12 | 16.20 | 16.13 |
| C-27 | 14.91 | 14.82 | 14.82 | 14.82 | 14.81 | 14.81 | 14.83 |
| C-28 | 177.59 | 173.73 | 173.79 | 173.99 | 173.85 | 173.90 | 173.83 |
| C-29 | 110.552 | 109.50 | 109.56 | 109.63 | 109.47 | 109.48 | 109.57 |
| C-30 | 19.54 | 19.88 | 19.85 | 19.82 | 19.86 | 19.87 | 19.86 |
| C-2' |  | 32.75 | 32.74 | 32.71 | 32.72 | 32.74 | 32.74 |
| C-3' |  | 50.81 | 49.29 | 47.37 | 45.82 | 44.15 | 48.56 |
| C-5' |  | 50.81 | 49.29 | 47.37 | 45.82 | 44.15 | 48.56 |
| C-6' |  | 32.75 | 32.74 | 32.71 | 32.72 | 32.74 | 32.74 |
| C-1" |  | 147.84 | 150.59 | 154.86 |  |  | 153.25 |
| C-2" |  | 118.38 d, (6.38 Hz)$^a$ | 130.75 | 113.19 | 159.57 | 161.956 | 115.06 |
| C-3" |  | 115.87 d, (18.37 Hz)$^a$ | 133.10 | 126.11 | 107.70 |  | 126.67 q (3.25 Hz)$^a$ |
| C-4" |  | 157.7 d, (199.1 Hz)$^a$ | 123.13 | 139.25 | 137.90 | 157.94 | 121.43 q (27.0 Hz)$^a$ |
| C-5" |  | 115.87 d, (18.37 Hz)$^a$ | 117.81 | 126.11 | 114.21 | 110.68 | 126.67 q (3.25 Hz)$^a$ |
| C-6" |  | 118.38 d, (6.38 Hz)$^a$ | 115.91 | 113.19 | 148.06 | 157.94 | 115.06 |
| C-7" |  |  |  |  |  |  | 124.80 q (224.38 Hz)$^a$ |

$^a$Values in parentheses are coupling constants in Hz with fluorine.

Example 8

An antibacterial test was carried out using the above-mentioned paper disc diffusion method. Betulonic acid amide was dissolved in DMSO to make a sample having a concentration of 1 mg/mL. A filter paper (diameter: 8 mm, manufactured by Advantec, Toyo Roshi Kaisha, Japan) wetted with 60 μL of the sample was attached to an agar plate, and then a circumference, around which bacteria were not cultivated, was measured. DMSO was used as a negative control, and gentamicin was used as a positive control. The antibacterial test was repeatedly carried out three times. *Ochrobactrum anthropi* KCTC 22833T and *Stenotrophomonas maltophilia* KCTC 1773T used in the antibacterial test were purchased from Korean Collection for Type Culture (KCTC), and *Ochrobactrum intermedium* KACC 11952T and *Stenotrophomonas nitritireducens* KACC 10891T used in the antibacterial test were purchased from Korean Agricultural Culture Collection (KACC). The diameters of clear circular zones of samples 2 to 7 of FIG. 1 were measured by a paper disc diffusion method, and compared to that of gentamicin. The results thereof are given in Table 3 below. From Table 3, it can be ascertained that sample 1 (4-(4'-fluorophenylpiperazin-1-yl) amide betulonic acid) provides a growth inhibition effect only to *Stenotrophomonas nitritireducens*, but other samples 2 to 7 provides growth inhibition effects to four kinds of bacteria. Particularly, it can be ascertained that the activity of sample 2 (4-(3',4'-dichlorophenylpiperazin-1-yl) amide betulonic acid) and the activity of sample 7 (4-(4'-trifluoromethylphenylpiperazin-1-yl) amide betulonic acid) are highest.

TABLE 3

Results of antibacterial test of betulonic acid amides

| | Antibacterial zone of inhibition (mm) | | | |
|---|---|---|---|---|
| Compound | O. anthropi | O. intermedium | S. nitritireducens | S. maltophila |
| 1 of FIG. 1 | — | — | 11 | — |
| 2 of FIG. 1 | 15 | 14 | 15 | 13 |
| 3 of FIG. 1 | 12 | 13 | 13 | 11 |
| 4 of FIG. 1 | 12 | 10 | 11 | 10 |

TABLE 3-continued

Results of antibacterial test of betulonic acid amides

| Compound | Antibacterial zone of inhibition (mm) | | | |
| --- | --- | --- | --- | --- |
| | O. anthropi | O. intermedium | S. nitritireducens | S. maltophila |
| 5 of FIG. 1 | 13 | 10 | 11 | 10 |
| 6 of FIG. 1 | 15 | 14 | 16 | 14 |
| Gentamicin | 19 | 17 | 21 | 16 |

Example 9

Step (I): Synthesis of Nα-butyloxycarbonyl-Nε-benzyloxycarbonyl-Lysin methyl ester (Boc-Lys(Cbz)-OMe) referred to the paper [Kobayashi et al., J. Org. Chem. 66:6626-6623(2001)]. 2 g of Nα-butyloxycarbonyl-Nε-benzyloxycarbonyl-Lysin (Boc-Lys(Cbz)-OH) was dissolved in 15 mL of trimethylsilydiazomethane, 10 mL of anhydrous methanol was added thereto, and then stirred at room temperature for 60 min. The reaction product was passed through 7.7 g of silica gel (Sigma Aldrich, Silical Davisil Grade 635, pore 60, 60-100 mesh) to obtain a filtrate. The filtrate was evaporated to obtain a light yellow Nα-butyloxycarbonyl-Nε-benzyloxycarbonyl-Lysin methyl ester (Boc-Lys(Cbz)-OMe).

Step (II): A total amount of Boc-Lys(Cbz)-OMe was dissolved in a mixed solvent of 40 ml of ethyl acetate and 40 ml of methanol, and then the resultant solution was stirred at room temperature for 4 hours under a hydrogen atmosphere while gradually adding 0.223 g of Pd/C. The reaction product was passed through 3.56 g of celite (Sigma Aldrich) to remove Pd/C, and was then washed with 20 ml of methanol (MeOH) two times to obtain a filtrate. The filtrate was evaporated to obtain light viscous solid Boc-Lys-OMe.

Step (III): The synthesis reaction of betulonic acid and Boc-Lys-OMe referred to the paper [Zhao et al., J. Org. Chem. 69:270-279(2004)]. A total amount of the Boc-Lys-OMe obtained in step (II) and 2 g of betulonic acid were dissolved in 60 ml of THF (tetrahydrofuran), and then 1127 mg of 1,3-dicyclohexylecarbodiimide (DCC), 754 mg of 1-hydroxybenzotriazole hydrate (HOBt) and 0.925 ml of triethylamine were added thereto. The resultant solution was stirred for 2 hours while maintaining the temperature of a reactor at 0° C.

When a white precipitate was generated in the reactor, the temperature of the reactor was maintained at room temperature, and the synthesis reaction of a Boc-Lys-BOA monomer ester was conducted. 0.2 ml of the synthesis reaction product was completely evaporated, dried and then dissolved in 0.94 ml of ethanol (EtOHD) to obtain a sample. The concentration of Boc-Lys-BOA monomer ester was analyzed while analyzing the sample using HPLC.

The sample extracted from the reactor was analyzed for 62 hours using a HPLC gradient elution method of Table 1 until the peak area of a component (retention time: 12.0 min) corresponding to Boc-lysinated betulonic acid monomer ester was not changed.

As the result of analysis of the sample, the sample includes impurities having an area ratio of the sample to Boc-Lys-BOA monomer ester of 7.85 and retention times of 3.5, 4.1, 15.15, 16.0 and 23.23 min in amounts of 50.39%, 3.1%, 0.68%, 32.68%, 2.97% and 2.31%, respectively (refer to FIG. 3).

Example 10

Purification of organic synthesis reaction product of Boc-Lysinated betulonic acid monomer ester and purification of hydrolysis reaction product of Boc-Lysinated betulonic acid monomer ester 3.37 g of white crystal (55), which is an organic synthesis reaction product of Boc-Lysinated betulonic acid mono ester, was dissolved in 600 ml of a mixed solvent of EtOAc:hexane (1:1, v/v) to make a sample (56), and then the sample (56) was passed through a column (90) filled with 40 g of aluminum oxide to decrease the concentration of a polar component having a retention time of 4 min to 5 min from 50.39% to 4.86~6.96%. 80 ml of a mixed solvent (57) of EtOAc:hexane (1:1, v/v) was supplied to an adsorption tower (90) to wash the sample. The solution (58) discharged from the adsorption tower (90) and the solution (59) discharged from a washing tower were evaporated and dried to obtain 2.825 g of white crystals (60), and then the white crystals (60) were treated with aluminum oxide to increase the concentration of Boc-Lysinated betulonic acid monomer ester from 7.85% to 14.6%. 2.825 g of the white crystals (60) were dissolved in 200 ml of ethanol (EtOH) to make a sample (61), and then the sample (61) was filtered to separate an insoluble white precipitate and remove 0.8096 g of a component (62) having a retention time of 15 min to obtain a first filtrate (63), and then ethanol (EtOH) was evaporated until the volume of the first filtrate (63) became 75 ml. Then, the first filtrate (63) was further filtered to remove 0.1134 g of a component (65) having a retention time of 15 min to obtain a second filtrate (66), and then ethanol (EtOH) was evaporated until the volume of the second filtrate (66) became 25 ml. Then, the second filtrate (66) was further filtered to remove 0.1324 g of a component (68) having a retention time of 15 min to obtain a third filtrate (69), and then the third filtrate (69) was completely evaporated to obtain 1.1845 g of white crystals (71), thus increasing the concentration of Boc-Lysinated betulonic acid monomer ester from 14.6% to 34.33%.

Figure 4:
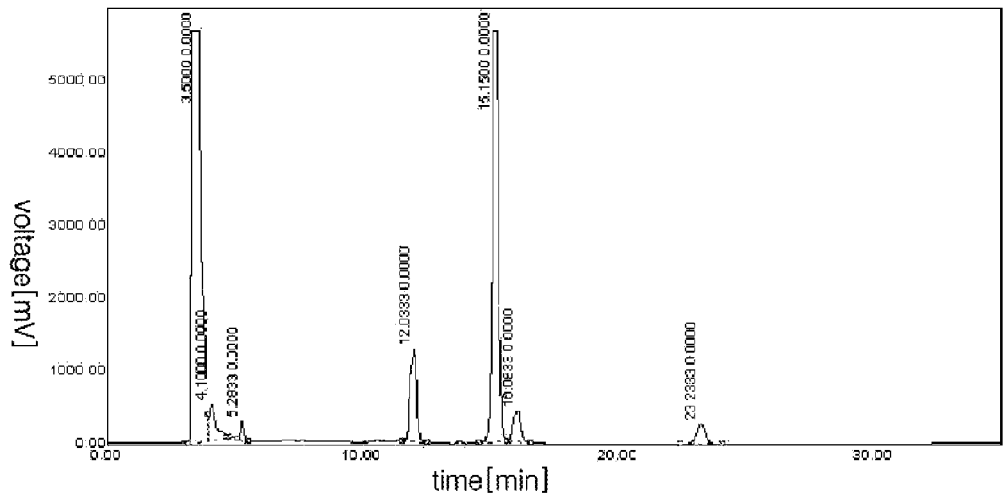
FIG. 4 is graph of HPLC analysis of a Boc-lysinated betulonic acid monomer ester (Boc-Lys-BOA monomer ester) according to an embodiment of the present invention.
Figure 5:
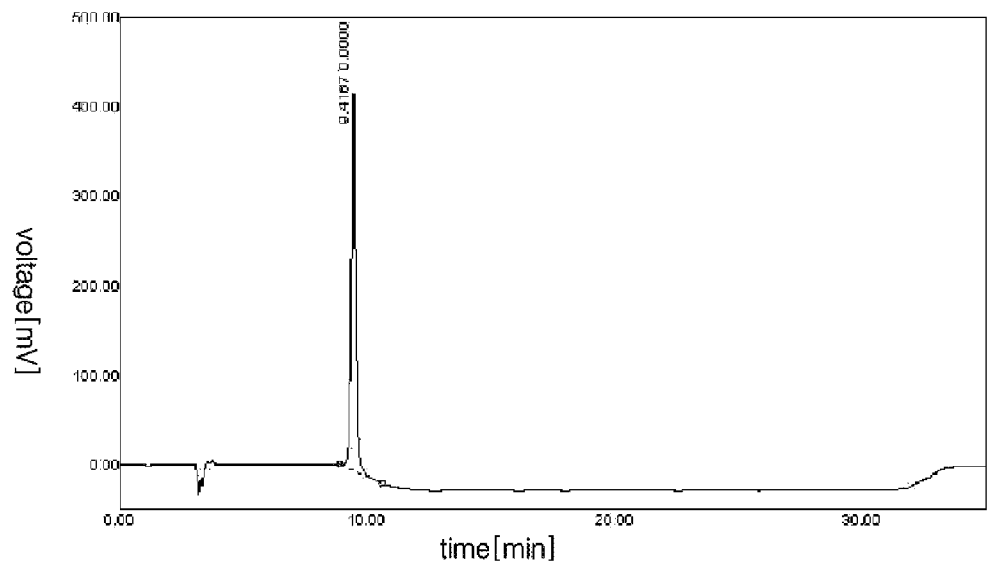
FIG. 5 is graph of HPLC analysis of Boc-lysinated betulonic acid (Boc-Lys-BOA) according to an embodiment of the present invention.

The white crystals (71) were dissolved in 25 ml of ethanol to make a sample (72), and then the sample (72) was introduced into a RP $C_{18}$ semi-preparative chromatography column (eluent MeCN:$H_2O$=86:14, v/v, 7 ml/min, 250 mm×21.1 mm) to collect a Boc-Lysinated betulonic acid monomer ester fraction, and then this Boc-Lysinated betulonic acid monomer ester fraction was evaporated and dried to obtain 0.6597 g of white powder (75) (referring to FIG. 4, Boc-Lys-BOA monomer ester purity>99%, yield to birch bark: 0.58 wt %).

256.1 mg of the white powder (75) having a Boc-Lys-BOA monomer ester purity of 99% or more was dissolved in 5 ml of tetrahydrofuran (THF), 18.28 mg of LiOH monohydrate and 0.767 ml of pure water were added thereto, and then the resultant solution was stirred at room temperature for 7 hours to hydrolyze methyl ester bonded to C-terminus of lysine. The hydrolysis reaction product (76) was evaporated and dried to obtain white solids (77). The obtained white solids (77) was dissolved in 15 ml of ethanol (EtOH) having the lowest LiOH solubility to make a sample (78). The sample (78) was filtered by a PTFE membrane and washed with 5 ml of −20° C. ethanol (EtOH) to remove insoluble LiOH (79) to obtain a filtrate (80). 20 ml of the filtrate (80) was introduced into a RP $C_{18}$ semi-preparative chromatography column (250 mm×21.1 mm, 10 µm, 100 Å, MeCN:$H_2O$=86:14 v/v, 7 ml/min). The solution discharged from the column was detected by a UV/VIS detector at 212 nm and 252 nm, and simultaneously a Boc-Lysinated betulonic acid fraction was separated from the solution. The Boc-Lysinated betulonic acid fraction was evaporated and dried to obtain white crystals (referring to FIG. 4, Boc-Lys-BOA monomer ester purity>99.5%, yield to birch bark: 0.47 wt %).

$C_{42}H_{68}N_2O_6$: Boc-lysinated betulonic acid monomer ester
$^1$H NMR (600 MHz, CDCl$_3$):

0.93 (3H, s, Me-25), 0.96 (3H, s, Me-27), 0.97 (3H, s, Me-26), 1.01 (1H, M, H-12), 1.02 (3H, s, Me-24), 1.06 (3H, s, Me-23), 1.06 (3H, s, Me-23), 1.14-1.58 (18H, m, H-1, 5, 6, 6, 7, 7, 9, 11, 11, 12, 15, 15, 16, 18, 21, 22, 33, 33), 1.45 (9H, br. s, H-40), 1.68 (3H, s, H-30), 1.73 (4H, m, H-1, 16, 21, 22), 1.91 (4H, m, H-32, 34), 2.39 (1H, m, H-2), 2.49 (2H, m, H-2, 13), 3.14 (1H, dt, J=11.4 Hz, J=4.8 Hz, H-19), 3.20 (1H, m, H-31), 3.25 (1H, m, H-31), 3.74 (3H, s, H-37), 4.29 (1H, m, H-35), 4.29 (1H, m, H-35), 4.74 and 4.59 (2H, both br. s, H-29), 5.06 (1H, d, J=7.8 Hz, H-42), 5.69 (1H, t, J=5.4 Hz, H-41).

TABLE 4

$^{13}$C NMR of Boc-Lysinated betulonic acid monomer ester

| C | BOA(betulonic acid) | Boc-Lys-BOA monomer ester |
|---|---|---|
| C-1 | 39.80 | 39.04 |
| C-2 | 34.33 | 34.37 |
| C-3 | 218.55 | 218.54 |
| C-4 | 47.54 | 47.55 |
| C-5 | 55.62 | 55.18 |
| C-6 | 19.82 | 19.83 |
| C-7 | 33.78 | 33.88 |
| C-8 | 40.82 | 39.83 |
| C-9 | 50.03 | 50.18 |
| C-10 | 37.25 | 37.10 |
| C-11 | 21.56 | 22.92 |
| C-12 | 26.67 | 25.79 |
| C-13 | 38.71 | 37.93 |
| C-14 | 42.68 | 42.70 |
| C-15 | 30.75 | 29.58 |
| C-16 | 32.31 | 33.95 |
| C-17 | 56.62 | 55.72 |
| C-18 | 49.36 | 50.23 |
| C-19 | 47.10 | 46.88 |
| C-20 | 150.52 | 151.11 |
| C-21 | 29.88 | 31.02 |
| C-22 | 37.11 | 38.63 |
| C-23 | 26.84 | 26.77 |
| C-24 | 21.20 | 21.23 |
| C-25 | 16.17a | 16.19 |
| C-26 | 16.02a | 16.16 |
| C-27 | 14.83 | 14.75 |
| C-28 | 182.80 | 177.97 |
| C-29 | 109.98 | 109.60 |
| C-30 | 19.57 | 19.68 |
| C-31 |  | 40.86 |
| C-32 |  | 31.02 |
| C-33 |  | 21.64 |
| C-34 |  | 32.68 |
| C-35 |  | 53.43 |
| C-36 |  | 173.47 |
| C-37 |  | 52.54 |
| C-38 |  | 155.63 |
| C-39 |  | 80.12 |
| C-40 |  | 28.52 |

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of purifying betulonic acid, comprising the steps of:
    a) injecting a Jones oxidation reagent ($CrO_3$/c-$H_2SO_4$/$H_2O$) into a mixed solution of acetone and betulin to obtain an organic synthesis reaction product and filtering and concentrating the obtained reaction product;
    b) introducing ethyl acetate into the concentrated reaction product to liquid-liquid extract betulonic acid
    c) introducing a saturated aqueous sodium chloride solution (brine) into the ethyl acetate solution, in which the extracted betulonic acid is dissolved, to wash the ethyl acetate solution and remove impurities therefrom;
    d) introducing hexane or petroleum ether, as a nonpolar solvent, into the ethyl acetate solution to remove nonpolar substances, passing the washed ethyl acetate solution through an adsorption tower filled with aluminum oxide or silica gel, as a polar adsorbent, to remove polar substances, and then drying the ethyl acetate solution to produce betulonic acid (purity: more than 92%, yield to birch bark: 2.75 wt %); and
    e) dissolving the produced betulonic acid in a mixed solvent of ethanol and acetonitrile, separating and treating the mixed solution using a semi-preparative chromatography column filled with $C_{18}$ stationary phase, and then drying the separated and treated mixed solution to produce high-purity betulonic acid (purity: more than 99.5%, yield to birch bark: 1.8 wt %).

2. The method of claim 1, wherein the step a) comprises the steps of:
    introducing methanol into the reaction product (1) and then filtering the reaction product to remove a blue precipitate ($Cr_2O_3$) and obtain a dark brown filtrate (2); and
    evaporating 40~50 vol % of the filtrate (2) to recover methanol and acetone (3).

3. The method of claim 1, wherein the step b) comprises the steps of:
    introducing ethyl acetate (5) into the concentrated reaction product (4) at a ratio of 1:1.3~2 (v/v) in a liquid-liquid extractor and then stirring the mixture to first extract betulonic acid from an upper ethyl acetate layer (6) in the liquid-liquid extractor; and
    introducing ethyl acetate (8) into a lower layer (7) of the liquid-liquid extractor at a ratio of 1:1~2 (v/v) to second extract betulonic acid from an upper ethyl acetate layer (9) in another liquid-liquid extractor.

4. The method of claim 1, wherein the step c) comprises the steps of:
    introducing a saturated aqueous sodium chloride solution (brine) (12) into the ethyl acetate solution (11), in which betulonic acid is dissolved, at a ratio of 2:1 (v/v) in a liquid-liquid extractor to first separate and remove impurities (14) from an lower layer of the liquid-liquid extractor; and
    introducing a saturated aqueous sodium chloride solution (brine) (15) into the ethyl acetate solution (13), in which the first washed betulonic acid is dissolved, at a ratio of 3~5:1 (v/v) in another liquid-liquid extractor to secondly separate and remove water-soluble impurities (15) from an lower layer of the liquid-liquid extractor.

5. The method of claim 1, wherein the step d) comprises the steps of:
    introducing hexane or petroleum ether, as a nonpolar solvent (18), into the washed ethyl acetate solution at a ratio of 1:1~5 (v/v) to precipitate green impurities, thus removing nonpolar substances;
    supplying an organic solvent, in which betulonic acid is dissolved, into at least one adsorption tower filled with a polar adsorbent (aluminum oxide or silica gel) to adsorb and remove impurities having higher polarity than betulonic acid, thus removing polar substances; and evaporating and drying the betulonic acid-containing solution having passed through the adsorption tower to produce white crystalline betulonic acid (purity: more than 92%, yield to birch bark: 2.75 wt %).

6. The method of claim 1, wherein the step e) is the step of: dissolving the produced betulonic acid in a mixed solvent of ethanol and acetonitrile (1:1 (v/v)) to obtain a sample, separating and treating the sample while supplying an eluent of acetonitrile and water (86:14 (v/v)) into a semi-preparative chromatography column filled with $C_{18}$ stationary phase at a flow velocity of 0.03~0.1 cm/sec, and then evaporating and drying the separated and treated sample to produce white crystalline betulonic acid (purity: more than 99.5%, yield to birch bark: 1.8 wt %).

7. A method of purifying Boc-lysinated betulonic acid using the high-purity betulonic acid obtained by the method of claim 5 as a starting material, comprising the steps of:
   a) dissolving an organic synthesis reaction product of a Boc-lysinated betulonic acid monomer ester in a mixed solvent of ethyl acetate and hexane (or petroleum ether) and then treating the resultant solution with an adsorption tower filed with aluminum oxide (or silica gel) to remove polar impurities;
   b) evaporating and drying the solution discharged from the adsorption tower to obtain white crystals, dissolving the white crystals in ethanol, crystallizing impurities in the resultant solution at 20~-2° C., and then filtering this solution to remove the crystallized impurities;
   c) evaporating and drying the filtrate to obtain crystals, dissolving the crystals in ethanol, and then fractionating the resultant solution using a reverse phase $C_{18}$ chromatography to obtain a Boc-lysinated betulonic acid monomer ester having a purity of 99% or more (yield to birch bark: 0.58 w %); and
   (d) dissolving the Boc-lysinated betulonic acid monomer ester in dichloromethane (DCM) or tetrahydrofuran (THF), adding sodium hydroxide (NaOH), lithium hydroxide (LiOH) or potassium hydroxide (KOH) thereto, hydrolyzing the resultant solution, and then fractionating the hydrolysis reaction product using a reverse phase $C_{18}$ chromatography to obtain Boc-lysinated betulonic acid (purity: more than 99.5%, yield to birch bark: 0.47 w %).

8. A method of purifying Boc-lysinated betulonic acid using the high-purity betulonic acid obtained by the method of claim 4 as a starting material, comprising the steps of:
   a) dissolving an organic synthesis reaction product of a Boc-lysinated betulonic acid monomer ester in a mixed solvent of ethyl acetate and hexane (or petroleum ether) and then treating the resultant solution with an adsorption tower filed with aluminum oxide (or silica gel) to remove polar impurities;
   b) evaporating and drying the solution discharged from the adsorption tower to obtain white crystals, dissolving the white crystals in ethanol, crystallizing impurities in the resultant solution at 20~-2° C., and then filtering this solution to remove the crystallized impurities;
   c) evaporating and drying the filtrate to obtain crystals, dissolving the crystals in ethanol, and then fractionating the resultant solution using a reverse phase $C_{18}$ chromatography to obtain a Boc-lysinated betulonic acid monomer ester having a purity of 99% or more (yield to birch bark: 0.58 w %); and
   (d) dissolving the Boc-lysinated betulonic acid monomer ester in dichloromethane (DCM) or tetrahydrofuran (THF), adding sodium hydroxide (NaOH), lithium hydroxide (LiOH) or potassium hydroxide (KOH) thereto, hydrolyzing the resultant solution, and then fractionating the hydrolysis reaction product using a reverse phase $C_{18}$ chromatography to obtain Boc-lysinated betulonic acid (purity: more than 99.5%, yield to birch bark: 0.47 w %).

9. A method of purifying Boc-lysinated betulonic acid using the high-purity betulonic acid obtained by the method of claim 3 as a starting material, comprising the steps of:
   a) dissolving an organic synthesis reaction product of a Boc-lysinated betulonic acid monomer ester in a mixed solvent of ethyl acetate and hexane (or petroleum ether) and then treating the resultant solution with an adsorption tower filed with aluminum oxide (or silica gel) to remove polar impurities;
   b) evaporating and drying the solution discharged from the adsorption tower to obtain white crystals, dissolving the white crystals in ethanol, crystallizing impurities in the resultant solution at 20~-2° C., and then filtering this solution to remove the crystallized impurities;
   c) evaporating and drying the filtrate to obtain crystals, dissolving the crystals in ethanol, and then fractionating the resultant solution using a reverse phase $C_{18}$ chromatography to obtain a Boc-lysinated betulonic acid monomer ester having a purity of 99% or more (yield to birch bark: 0.58 w %); and
   (d) dissolving the Boc-lysinated betulonic acid monomer ester in dichloromethane (DCM) or tetrahydrofuran (THF), adding sodium hydroxide (NaOH), lithium hydroxide (LiOH) or potassium hydroxide (KOH) thereto, hydrolyzing the resultant solution, and then fractionating the hydrolysis reaction product using a reverse phase $C_{18}$ chromatography to obtain Boc-lysinated betulonic acid (purity: more than 99.5%, yield to birch bark: 0.47 w %).

10. A method of purifying Boc-lysinated betulonic acid using the high-purity betulonic acid obtained by the method of claim 2 as a starting material, comprising the steps of:
    a) dissolving an organic synthesis reaction product of a Boc-lysinated betulonic acid monomer ester in a mixed solvent of ethyl acetate and hexane (or petroleum ether) and then treating the resultant solution with an adsorption tower filed with aluminum oxide (or silica gel) to remove polar impurities;
    b) evaporating and drying the solution discharged from the adsorption tower to obtain white crystals, dissolving the white crystals in ethanol, crystallizing impurities in the resultant solution at 20~-2° C., and then filtering this solution to remove the crystallized impurities;
    c) evaporating and drying the filtrate to obtain crystals, dissolving the crystals in ethanol, and then fractionating the resultant solution using a reverse phase $C_{18}$ chromatography to obtain a Boc-lysinated betulonic acid monomer ester having a purity of 99% or more (yield to birch bark: 0.58 w %); and
    (d) dissolving the Boc-lysinated betulonic acid monomer ester in dichloromethane (DCM) or tetrahydrofuran (THF), adding sodium hydroxide (NaOH), lithium hydroxide (LiOH) or potassium hydroxide (KOH) thereto, hydrolyzing the resultant solution, and then fractionating the hydrolysis reaction product using a reverse phase $C_{18}$ chromatography to obtain Boc-lysinated betulonic acid (purity: more than 99.5%, yield to birch bark: 0.47 w %).

11. A method of purifying Boc-lysinated betulonic acid using the high-purity betulonic acid obtained by the method of claim 1 as a starting material, comprising the steps of:

a) dissolving an organic synthesis reaction product of a Boc-lysinated betulonic acid monomer ester in a mixed solvent of ethyl acetate and hexane (or petroleum ether) and then treating the resultant solution with an adsorption tower filed with aluminum oxide (or silica gel) to remove polar impurities;

b) evaporating and drying the solution discharged from the adsorption tower to obtain white crystals, dissolving the white crystals in ethanol, crystallizing impurities in the resultant solution at 20~−2° C., and then filtering this solution to remove the crystallized impurities;

c) evaporating and drying the filtrate to obtain crystals, dissolving the crystals in ethanol, and then fractionating the resultant solution using a reverse phase $C_{18}$ chromatography to obtain a Boc-lysinated betulonic acid monomer ester having a purity of 99% or more (yield to birch bark: 0.58 w %); and (d) dissolving the Boc-lysinated betulonic acid monomer ester in dichloromethane (DCM) or tetrahydrofuran (THF), adding sodium hydroxide (NaOH), lithium hydroxide (LiOH) or potassium hydroxide (KOH) thereto, hydrolyzing the resultant solution, and then fractionating the hydrolysis reaction product using a reverse phase $C_{18}$ chromatography to obtain Boc-lysinated betulonic acid (purity: more than 99.5%, yield to birch bark: 0.47 w %).

\* \* \* \* \*